(12) United States Patent
Herne

(10) Patent No.: US 7,993,848 B2
(45) Date of Patent: Aug. 9, 2011

(54) STAPHYLOCOCCUS PROTEIN A DOMAIN MUTANTS THAT BIND TO TNF-α

(75) Inventor: **

FIGURE 1A

| Polypeptide | Amino acid sequence | | | | | | SEQ ID NO: |
|---|---|---|---|---|---|---|---|
| Z00000 | VDNKFNKEQQ | NAFYEILHLP | NLNEEQRNAF | IQSLKDDPSQ | SANLLAEAKK | LNDAQAPK | 1 |
| Z00182 | VDNKFNKEAA | WAPFEIQHLP | NLNHPQNDAF | IDSLTDDPSQ | SANLLAEAKK | LNDAQAPK | 2 |
| Z00183 | VDNKFNKEMF | GAVGEIGALP | NLNDRQLRAF | ILSLWDDPSQ | SANLLAEAKK | LNDAQAPK | 3 |
| Z00184 | VDNKFNKECW | RAPFEIYRLP | NLNREQQIAF | IRSLCDDPSQ | SANLLAEAKK | LNDAQAPK | 4 |
| Z00185 | VDNKFNKELG | WAIGEIGTLP | NLNHQQFRAF | ILSLWDDPSQ | SANLLAEAKK | LNDAQAPK | 5 |
| Z00186 | VDNKFNKESE | GAMHEIVRLP | NLNAWQRQAF | IVSLWDDPSQ | SANLLAEAKK | LNDAQAPK | 6 |
| Z00187 | VDNKFNKEKK | MAACEIQGLP | NLNIDQCWAF | ITSLRDDPSQ | SANLLAEAKK | LNDAQAPK | 7 |
| Z00188 | VDNKFNKEMQ | CAGCEIQDLP | NLNIEQCCAF | IRSLRDDPSQ | SANLLAEAKK | LNDAQAPK | 8 |
| Z00189 | VDNKFNKEGR | TAACEIQDLP | NLNLDQCWAF | IKSLLDDPSQ | SANLLAEAKK | LNDAQAPK | 9 |
| Z00190 | VDNKFNKECS | MAPREIWALP | NLNREQAVAF | IRSLCDDPSQ | SANLLAEAKK | LNDAQAPK | 10 |
| Z00191 | VDNKFNKECR | TAPREIFSLP | NLNIGQQWAF | IRSLCDDPSQ | SANLLAEAKK | LNDAQAPK | 11 |
| Z00192 | VDNKFNKETV | PAMREIASLP | NLNTTQKVAF | IRSLSDDPSQ | SANLLAEAKK | LNDAQAPK | 12 |
| Z00193 | VDNKFNKECA | YAPREIWRLP | NLNHQQGVAF | IRSLCDDPSQ | SANLLAEAKK | LNDAQAPK | 13 |
| Z00194 | VDNKFNKEPN | VASMEILPLP | NLNQQMTAF | IQSLDDDPSQ | SANLLAEAKK | LNDAQAPK | 14 |
| Z00195 | VDNKFNKERV | AAACEIESLP | NLNLQQCWAF | IRSIMDDPSQ | SANLLAEAKK | LNDAQAPK | 15 |
| Z00196 | VDNKFNKECF | MAPQEINKLP | NLNAWQKYAF | IWSLCDDPSQ | SANLLAEAKK | LNDAQAPK | 16 |
| Z00197 | VDNKFNKEQS | SAMREIVQLP | NLNPLQRAAF | IHSLWDDPSQ | SANLLAEAKK | LNDAQAPK | 17 |
| Z00198 | VDNKFNKEFV | YAIAEIMNLP | NLNQSQQLAF | IYSLRDDPSQ | SANLLAEAKK | LNDAQAPK | 18 |
| Z00199 | VDNKFNKEKQ | IAACEIMDLP | NLNQDQCFAF | IRSLRDDPSQ | SANLLAEAKK | LNDAQAPK | 19 |
| Z00200 | VDNKFNKEKG | RATGEIGALP | NLNPQQYRAF | ILSLHDDPSQ | SANLLAEAKK | LNDAQAPK | 20 |
| Z00201 | VDNKFNKEHM | EADCEIEHLP | NLNRKQCWAF | IKSLRDDPSQ | SANLLAEAKK | LNDAQAPK | 21 |
| Z00202 | VDNKFNKERT | VASCEIEHLP | NLNLDQCWAF | IDSLRDDPSQ | SANLLAEAKK | LNDAQAPK | 22 |
| Z00203 | VDNKFNKESA | HAVGEIGSLP | NLNIVQIGAF | IKSLWDDPSQ | SANLLAEAKK | LNDAQAPK | 23 |
| Z00204 | VDNKFNKEGR | PAGLEIMCLP | NLNTAQMVAF | IRSLTDDPSQ | SANLLAEAKK | LNDAQAPK | 24 |
| Z00205 | VDNKFNKESA | HAIGEIANLP | NLNGGQLRAF | ILSLLDDPSQ | SANLLAEAKK | LNDAQAPK | 25 |
| Z00206 | VDNKFNKERQ | QALGEISALP | NLNLHQYYAF | IRSLLDDPSQ | SANLLAEAKK | LNDAQAPK | 26 |
| Z00207 | VDNKFNKEIV | YAPREIFHLP | NLNLIQQIAF | IRSLLDDPSQ | SANLLAEAKK | LNDAQAPK | 27 |
| Z00208 | VDNKFNKESN | KAPCEIQDLP | NLNIDQCIAF | IRSLRDDPSQ | SANLLAEAKK | LNDAQAPK | 28 |
| Z00209 | VDNKFNKEFH | GALREIWKLP | NLNVRQAMAF | IRSLIDDPSQ | SANLLAEAKK | LNDAQAPK | 29 |

FIGURE 1B

| | | | | | | |
|---|---|---|---|---|---|---|
| Z00210 | VDNKFNKEVL | QAPQEIHRLP | NLNLIQKMAF | IRSLMDDPSQ | SANLLAEAKK | LNDAQAPK | 30 |
| Z00211 | VDNKFNKEMH | LALQEIYALP | NLNIAQSVAF | IRSLVDDPSQ | SANLLAEAKK | LNDAQAPK | 31 |
| Z00212 | VDNKFNKEGY | KALGEIGRLP | NLNAQQFRAF | ILSLWDDPSQ | SANLLAEAKK | LNDAQAPK | 32 |
| Z00468 | VDNKFNKESP | GALSEIMALP | NLNVHQYYAF | IRSLLDDPSQ | SANLLAEAKK | LNDAQAPK | 33 |
| Z00732 | VDNKFNKESM | SAALEITRLP | NLNVHQYYAF | ITSLRDDPSQ | SANLLAEAKK | LNDAQAPK | 34 |
| Z00683 | VDNKFNKEFV | SAPREIHGLP | NLNVTQRMAF | IRSLLDDPSQ | SANLLAEAKK | LNDAQAPK | 35 |
| Z00684 | VDNKFNKECW | MAPKEIYRLP | NLNDWQRSAF | IRSLCDDPSQ | SANLLAEAKK | LNDAQAPK | 36 |
| Z00685 | VDNKFNKEGR | GARMEIVCLP | NLNWRQTVAF | IRSLQDDPSQ | SANLLAEAKK | LNDAQAPK | 37 |
| Z00734 | VDNKFNKEGH | QALVEIFRLP | NLNVQQATAF | IRSLVDDPSQ | SANLLAEAKK | LNDAQAPK | 38 |
| Z00735 | VDNKFNKEVT | VAGVEIGQLP | NLNLHQYYAF | ILSLLDDPSQ | SANLLAEAKK | LNDAQAPK | 39 |
| Z00736 | VDNKFNKEVH | QALREIFQLP | NLNLDQSIAF | IRSLADDPSQ | SANLLAEAKK | LNDAQAPK | 40 |
| Z00739 | VDNKFNKETA | QALGEIGVLP | NLNAQQAAAF | ILSLWDDPSQ | SANLLAEAKK | LNDAQAPK | 41 |
| Z00741 | VDNKFNKEGH | MAVREIHGLP | NLNVAQRMAF | IRSLVDDPSQ | SANLLAEAKK | LNDAQAPK | 42 |
| Z00744 | VDNKFNKEVA | QAVGEIGLLP | NLNALQFRAF | ILSLLDDPSQ | SANLLAEAKK | LNDAQAPK | 43 |
| Z00745 | VDNKFNKETQ | QAVLEIGTLP | NLNIHQYYAF | IKSLLDDPSQ | SANLLAEAKK | LNDAQAPK | 44 |
| Z00746 | VDNKFNKEKL | HAAQEIGRLP | NLNVHQYYAF | ITSLSDDPSQ | SANLLAEAKK | LNDAQAPK | 45 |
| Z00749 | VDNKFNKEVA | AAVGEIGSLP | NLNVGQFAAF | IRSLWDDPSQ | SANLLAEAKK | LNDAQAPK | 46 |
| Z00752 | VDNKFNKEVV | GAMLEIARLP | NLNRGQVNAF | IWSLADDPSQ | SANLLAEAKK | LNDAQAPK | 47 |
| Z00754 | VDNKFNKESW | QAVPEIFRLP | NLNVQQSIAF | IRSLVDDPSQ | SANLLAEAKK | LNDAQAPK | 48 |
| Z00767 | VDNKFNKELE | RAIFEISNLP | NLNLHQYYAF | ITSLQDDPSQ | SANLLAEAKK | LNDAQAPK | 49 |
| Z00769 | VDNKFNKEPL | AAVMEIVQLP | NLNLHQYYAF | IRSLNDDPSQ | SANLLAEAKK | LNDAQAPK | 50 |
| Z00770 | VDNKFNKETE | WAIAEIIGLP | NLNMHQYYAF | IMSLRDDPSQ | SANLLAEAKK | LNDAQAPK | 51 |
| Z00771 | VDNKFNKEAY | TASLEIANLP | NLNMHQYYAF | IHSLLDDPSQ | SANLLAEAKK | LNDAQAPK | 52 |
| Z00772 | VDNKFNKEMR | WAALEIAALP | NLNVHQYYAF | IRSLLDDPSQ | SANLLAEAKK | LNDAQAPK | 53 |
| Z00773 | VDNKFNKEFH | GAIREIHLLP | NLNLQQRMAF | IISLTDDPSQ | SANLLAEAKK | LNDAQAPK | 54 |
| Z00774 | VDNKFNKEWK | AAAREIGSLP | NLNLHQYYAF | IVSLQDDPSQ | SANLLAEAKK | LNDAQAPK | 55 |
| Z00775 | VDNKFNKETE | QAAWEIAILP | NLNWDQMAAF | IRSLIDDPSQ | SANLLAEAKK | LNDAQAPK | 56 |
| Z00776 | VDNKFNKEDR | RAPGEIVRLP | NLNPRQRAAF | IVSLRDDPSQ | SANLLAEAKK | LNDAQAPK | 57 |
| Z00777 | VDNKFNKETA | RAAHEIVRLP | NLNDRQLAAF | IVSLIVDDPSQ | SANLLAEAKK | LNDAQAPK | 58 |
| Z00778 | VDNKFNKEMF | SAIGEIGNLP | NLNDRQLAAF | ILSLFDDPSQ | SANLLAEAKK | LNDAQAPK | 59 |
| Z00779 | VDNKFNKETF | HAIGEIGSLP | NLNDMQFSAF | IISLWDDPSQ | SANLLAEAKK | LNDAQAPK | 60 |
| Z00780 | VDNKFNKENR | EAIVEIAELP | NLNMHQYYAF | IRSLLDDPSQ | SANLLAEAKK | LNDAQAPK | 61 |

FIGURE 1C

| | | | | | | |
|---|---|---|---|---|---|---|
| Z00781 | VDNKFNKEGS | KAIMEIIRLP | NLNVHQYVAF | IMSLRDDPSQ | SANLLAEAKK | LNDAQAPK | 62 |
| Z00782 | VDNKFNKEAP | GATSEINILP | NLNWRQIMAF | IVSLRDDPSQ | SANLLAEAKK | LNDAQAPK | 63 |
| Z00784 | VDNKFNKEFI | DAPREIIRLP | NLNMTQQMAF | IRSLADDPSQ | SANLLAEAKK | LNDAQAPK | 64 |
| Z00785 | VDNKFNKETM | AAMNEIVRLP | NLNGWQRYAF | IQSLRDDPSQ | SANLLAEAKK | LNDAQAPK | 65 |
| Z00786 | VDNKFNKEAH | SALREIIKLP | NLNIEQWQAF | IRSLADDPSQ | SANLLAEAKK | LNDAQAPK | 66 |
| Z00223 | VDNKFNKEWH | DALREIHRLP | NLNVYQSLAF | IRSLVDDPSQ | SANLLAEAKK | LNDAQAPK | 67 |
| Z00224 | VDNKFNKELY | YAKLEIANLP | NLNVHQWYAF | IISLEDDPSQ | SANLLAEAKK | LNDAQAPK | 68 |
| Z00225 | VDNKFNKEVR | FAIGEIGGLP | NLNDRQLRAF | ILSLWDDPSQ | SANLLAEAKK | LNDAQAPK | 69 |
| Z00227 | VDNKFNKEWE | WASKEIVILP | NLNTQQRAAF | IRSLWDDPSQ | SANLLAEAKK | LNDAQAPK | 70 |
| Z00235 | VDNKFNKETA | RATGEIAGLP | NLNIVQFRAF | ILSLWDDPSQ | SANLLAEAKK | LNDAQAPK | 71 |
| Z00237 | VDNKFNKEGR | NAVWEIAELP | NLNLHQYYAF | ITSLRDDPSQ | SANLLAEAKK | LNDAQAPK | 72 |
| Z00238 | VDNKFNKETA | QAPLEIALLP | NLNWPQKVAF | IRSLADDPSQ | SANLLAEAKK | LNDAQAPK | 73 |
| Z00243 | VDNKFNKEVF | WAAGEIGILP | NLNHMQYRAF | ILSLWDDPSQ | SANLLAEAKK | LNDAQAPK | 74 |
| Z00552 | VDNKFNKEQL | SAMLEITRLP | NLNTAQRPAF | IWSLADDPSQ | SANLLAEAKK | LNDAQAPK | 75 |
| Z01446 | VDNKFNKELG | WAIGEIGTLP | NLNHQQFRAF | ILSLWVDPSQ | SANLLAEAKK | LNDAQAPK | 76 |
| Z01447 | VDNKFNKENA | RAIEEIITLP | NLNKTQRAAF | ISSLTDDPSQ | SANLLAEAKK | LNDAQAPK | 77 |
| Z01608 | VDNKFNKEGP | GAVHEIVRLP | NLNPTQRVAF | IYSLRDDPSQ | SANLLAEAKK | LNDAQAPK | 78 |
| Z01609 | VDNKFNKESL | VAAREIGVLP | NLNSSQKKAF | IESLGDDPSQ | SANLLAEAKK | LNDAQAPK | 79 |
| Z01610 | VDNKFNKEAG | VAVGEIGMLP | NLNALQKGAF | IKSLFDDPSQ | SANLLAEAKK | LNDAQAPK | 80 |
| Z01611 | VDNKFNKESA | CATVEIGNLP | NLNLAQYRAF | ILSLRDDPSQ | SANLLAEAKK | LNDAQAPK | 81 |
| Z01612 | VDNKFNKERR | PADCEIWSLP | NLNRSQCFAF | IKSLRDDPSQ | SANLLAEAKK | LNDAQAPK | 82 |
| Z01613 | VDNKFNKETG | RAVGEIGFLP | NLNAYQASVF | IRSLWDDPSQ | SANLLAEAKK | LNDAQAPK | 83 |
| Z01614 | VDNKFNKEGH | MATVEIATLP | NLNGAQKKAF | IESLFDDPSQ | SANLLAEAKK | LNDAQAPK | 84 |
| TNF-α | VRSSSRTPSD | KPVAHVVANP | QAEGQLQWLN | RRANALLANG | VELRDNQLVV | PSEGLYLIYS | 85 |
| | QVLFKGQGCP | STHVLLTHTI | SRIAVSYQTK | VNLLSAIKSP | CQRETPEGAE | AKPWYEPIYL | |
| | GGVEQLEKGD | RLSAEINRPD | YLDFAESGQV | YFGIIAL | | | |

His₆-ZTNF-Cys

MGSSHHHHHHLQ | ZTNF | VDC

FIGURE 2

A: MGSSHHHHHHLQ | Z00734 | Z00734 | Z00734 | VDC

B: MGSSHHHHHHLQ | Z00752 | Z00752 | Z00752 | VDC

C: MGSSHHHHHHLQ | Z00771 | Z00771 | Z00771 | VDC

FIGURE 4

STAPHYLOCOCCUS PROTEIN A DOMAIN MUTANTS THAT BIND TO TNF-α

CROSS-REFERENCE TO RELATED APPLICATIONS

This application is a US National Stage application of International Patent Application Serial No. PCT/EP2006/002069 filed 1 Mar. 2006.

FIELD OF THE INVENTION

The present invention relates to a new polypeptide, which binds to tumour necrosis factor α, TNF-α, and to the use of such a polypeptide in a method of affinity separation, for example in a method for reducing the content of TNF-α in a body fluid, in processes for the production of recombinant TNF-α and in other applications. The polypeptide is related to a domain of staphylococcal protein A (SPA), in that the sequence of the polypeptide corresponds to the sequence of the SPA domain having at least one and at most about 20 substitution mutations.

BACKGROUND

Affibody® Molecules

Molecules related to protein Z, derived from domain B of staphylococcal protein A (SPA) (Nilsson B et al (1987) Protein Engineering 1, 107-133), have been selected from a library of randomized such molecules using different interaction targets (see e g WO95/19374; WO00/63243; Nord K et al (1995) Prot Eng 8:601-608; Nord K et al (1997) Nature Biotechnology 15, 772-777). Different target molecules have been used to select such protein Z derivatives, e g as described in Nord K et al (1997, supra). The experiments described in this reference outline principles of the general technology of selecting protein Z derivatives against given targets, rather than being a study directed towards the express objective of obtaining a molecule with high enough affinity for use in a specific therapeutic or biotechnological application.
TNF-α and its Role in Disease Tumor necrosis factor α, abbreviated as "TNF-α", is an important mammalian cytokine, which is involved in systemic inflammation and acute phase response. In humans, it is a 157 amino acid glycoprotein hormone, which is derived through cleavage of a 233 amino acid long propeptide (SwissProt entry P01375; Pennica et al, Nature 312:724-729 (1984); Wang et al, Science 228:149-154 (1985)). Some cells secrete shorter or longer isoforms of TNF-α. TNF-α has historically also been known as "cachexin" or "cachectin".

TNF-α is released by white blood cells, endothelial cells and several other tissue cells upon damage to the tissue, such as during infections. It acts on a variety of organ systems, such as the hypothalamus, where it inter alia stimulates the release of corticotropin-releasing hormone and suppresses appetite, and the liver, where it stimulates the acute phase response leading to an increase in C-reactive protein and other mediators. Among its many effects, TNF-α also increases insulin resistance.

Interfering with TNF-α and its function is an important approach in the development of pharmaceuticals for treatment of autoimmune disorders such as rheumatoid arthritis and psoriasis. Monoclonal antibodies that bind TNF-α have been developed, and such antibodies are commercially available as drugs. Examples are those bearing the INN names infliximab (Remicade®) and adalimumab (Humira®; see e.g. WO97/29131). TNF-α binding antibodies are described in e.g. WO91/02078. Also, a recombinant, soluble TNF-α receptor fused to an Fc portion of an IgG anti-body molecule has been developed as a pharmaceutical, and is known as etanercept (Enbrel®; see e g WO94/06476).

Recent developments of TNF-α binding antibodies and antibody derivatives are exemplified by WO2004/003019, which describes an antibody-derived "domain antibody ligand" with an affinity for TNF-α.
Drawbacks of TNF-α Binding Antibodies Whether the object is to find a novel therapeutic strategy for treating diseases in which interfering with TNF-α function is of importance, to establishing novel methods for the separation of TNF-α from other constituents in a sample, or some other application relying on TNF-α binding, the provision of molecules having a binding affinity for TNF-α is critical. Previously known antibodies and antibody related derivatives against TNF-α are not always the optimal choice, due to the complexity and relatively large size of the antibody molecule. Thus, there is a continued need for novel and alternative molecules with a high affinity for TNF-α, which can be used as reagents in various assays and processes where such an affinity is needed.

DISCLOSURE OF THE INVENTION

It is an object of the present invention to meet this need through the provision of a polypeptide that exhibits binding to TNF-α.

A related object of the invention is a TNF-α binding polypeptide which exhibits little or no non-specific binding.

It is another object of the invention to provide a TNF-α binding polypeptide that can readily be used as a moiety in a fusion polypeptide.

Another object is the provision of a TNF-α binding polypeptide, which does not exhibit the known problems of stability experienced with antibody reagents, but provides a stable and robust structure with the ability to withstand harsh environmental conditions.

Furthermore, it is an object to provide TNF-α binding polypeptide, the properties of which enable easy coupling thereof to a solid support or other matrix.

A related object is to provide a TNF-α binding polypeptide, which enables efficient separation of TNF-α from other constituents of a sample. Preferably, such a polypeptide is also useful for reducing the content of TNF-α in a body fluid of a human.

It is also an object to provide a molecule which can be used as a reagent for the detection of TNF-α at a low detection limit.

These and other objects are met by the present invention. Thus, in a first aspect, the invention provides a TNF-α binding polypeptide, which is related to a domain of staphylococcal protein A (SPA) in that the sequence of the polypeptide corresponds to the sequence of the SPA domain having 1 to about 20 substitution mutations.

In accordance herewith, the present inventors have found that it is possible to obtain a TNF-α binding polypeptide through substitution mutagenesis of a domain from SPA. An embodiment of the polypeptide of the invention may have the ability to interact with TNF-α with an apparent $K_D$ value of at most $1\times10^{-7}$ M as measured by surface plasmon resonance. Preferably, the polypeptide of the invention has the ability to interact with TNF-α with an apparent $K_D$ value of at most $5\times10^{-8}$ M as measured by surface plasmon resonance. More preferably, the polypeptide of the invention has the ability to interact with TNF-α with an apparent $K_D$ value of at most $1 \times 10^{-8}$ M as measured by surface plasmon resonance.

"Tumor necrosis factor α" or "TNF-α" refers to a mammalian glycoprotein hormone. The human form thereof is a 157 amino acid protein, which is derived through cleavage of a 233 amino acids large propeptide (SwissProt entry P01375; Pennica et al, Nature 312:724-729 (1984); Wang et al, Science 228:149-154 (1985)). The sequence of human TNF-α is given in SEQ ID NO:85. However, the TNF-α binding polypeptides of the present invention may also bind to other forms of TNF-α than the human form represented by SEQ ID NO:85. Thus, "TNF-α" or "tumor necrosis factor α" encompasses analogues of this cytokine in other organisms, as well as other forms of the protein in humans.

"Binding affinity for TNF-α" refers to a property of a polypeptide which may be tested e.g. by the use of surface plasmon resonance technology, such as in a Biacore® instrument. TNF-α binding affinity may be tested in an experiment wherein the polypeptide to be tested is immobilized on a sensor chip of the instrument, and a sample containing TNF-α is passed over the chip. The skilled person may then interpret the sensorgrams obtained to establish at least a qualitative measure of the polypeptide's binding affinity for TNF-α. If a quantitative measure is sought, for example with the purpose to establish a certain apparent $K_D$ value for the interaction, it is again possible to use surface plasmon resonance methods. Binding values may for example be defined in a Biacore® 2000 instrument (Biacore AB). The polypeptide to be tested may be immobilized on a sensor chip of the instrument, and samples of TNF-α prepared by serial dilution and injected in a random order. Apparent $K_D$ values may then be calculated from the results, using e.g. the 1:1 Langmuir binding model of the BIAevaluation 3.2 software provided by the instrument manufacturer. Binding specificity for TNF-α may also be tested by conventional methods. The testing of the binding specificity of polypeptides in accordance with the invention for TNF-α compared to Human Serum Albumin (HSA) and Immunoglobulin G (IgG) is described below.

The polypeptide according to the invention may be useful in any method relying on affinity for TNF-α of a reagent. Thus, the polypeptide may be used as a detection reagent, a capture reagent or a separation reagent in such methods. Methods that employ the polypeptide according to the invention in vitro may be performed in different formats, such as in microtitre plates, in protein arrays, on biosensor surfaces, on tissue sections, and so on. Different modifications of, and/or additions to, the polypeptide according to the invention may be performed in order to tailor the polypeptide to the specific use intended, without departing from the scope of the present invention. Such modifications and additions are described in more detail below, and may comprise additional amino acids comprised in the same polypeptide chain, or labels and/or therapeutic agents that are chemically conjugated or otherwise bound to the polypeptide according to the invention. Furthermore, the invention also encompasses fragments of the polypeptide that retain the capability of binding to TNF-α.

As stated above, the sequence of the polypeptide according to the present invention is related to an SPA domain sequence in that 1 to about 20 amino acid residues of said SPA domain have been substituted for other amino acid residues. However, the substitution mutations introduced should not affect the basic structure of the polypeptide. That is, the overall folding of the $C_\alpha$ backbone of the polypeptide of the invention will be substantially the same as that of the SPA domain to which it is related, e.g. having the same elements of secondary structure in the same order etc. Thus, polypeptides fall under the definition of having the same fold as the SPA domain if the basic structural properties are shared, those properties e.g. resulting in similar CD spectra. The skilled person is aware of other parameters that are relevant. This requirement of essentially conserving the basic structure of the SPA domain, upon mutation thereof, places restrictions on what positions of the domain may be subject to substitution. When starting from the known structure of the Z protein, for example, it is preferred that amino acid residues located on the surface of the Z protein may be substituted, whereas amino acid residues buried within the core of the Z protein "three-helix bundle" should be kept constant in order to preserve the structural properties of the molecule. The same reasoning applies to other SPA domains, and to the case when a fragment of an SPA domain is used.

The invention also encompasses polypeptides in which a TNF-α binding polypeptide described above is present as a TNF-α binding domain, to which additional amino acid residues have been added at one or both termini. These additional amino acid residues may play a role in the binding of TNF-α by the polypeptide, but may equally well serve other purposes, related for example to one or more of the production, purification, stabilization, coupling or detection of the polypeptide. Such additional amino acid residues may comprise one or more amino acid residues added for purposes of chemical coupling, e.g. to a chromatographic resin to obtain an affinity matrix. An example of this is the addition of a cysteine residue at the very first or very last position in the polypeptide chain, i.e. at the N or C terminus. Such additional amino acid residues may also comprise a "tag" for purification or detection of the polypeptide, such as a hexahistidyl ($His_6$) tag, or a "myc" ("c-Myc") tag or a "flag" tag for interaction with antibodies specific to the tag. The skilled person is aware of other alternatives.

The "additional amino acid residues" discussed above may also constitute one or more polypeptide domain(s) with any desired function, such as the same binding function as the first, TNF-α binding domain, or another binding function, or an enzymatic function, or a fluorescent function, or mixtures thereof.

Thus, the invention encompasses multimers of the polypeptide with affinity for TNF-α. It may be of interest, e.g. in a method of purification of TNF-α, to obtain even stronger binding of TNF-α than is possible with one polypeptide according to the invention. In this case, the provision of a multimer, such as a dimer, trimer or tetramer, of the polypeptide may provide the necessary avidity effects. The multimer may consist of a suitable number of polypeptides according to the invention. These polypeptide domains according to the invention, forming monomers in such a multimer, may all have the same amino acid sequence, but it is equally possible that they have different amino acid sequences. The linked polypeptide "units" in a multimer according to the invention may be connected by covalent coupling using known organic chemistry methods, or expressed as one or more fusion polypeptides in a system for recombinant expression of polypeptides, or joined in any other fashion, directly or mediated by a linker comprising a number of amino acids.

Additionally, "heterogenic" fusion polypeptides, in which a TNF-α binding polypeptide constitutes a first domain, or first moiety, and the second and further moieties have other functions than binding TNF-α, are also contemplated and fall within the ambit of the present invention. The second and further moiety/moieties of the fusion polypeptide may comprise a binding domain with affinity for another target molecule than TNF-α. Such a binding domain may well also be related to an SPA domain through substitution mutation at 1 to about 20 positions thereof. The result is then a fusion polypeptide having at least one TNF-α-binding domain and at least one domain with affinity for said other target molecule, in which both domains are related to an SPA domain. This makes it possible to create multispecific reagents that may be used in several biotechnological applications. The preparation of such multispecific multimers of SPA domain related polypeptides, in which at least one polypeptide domain has affinity for TNF-α, may be effected as described above for the multimer of several TNF-α binding "units". In other alternatives, the second or further moiety or moieties may comprise an unrelated, naturally occurring or recombinant, protein (or a fragment thereof retaining the binding capability of the naturally occurring or recombinant protein) having a binding affinity for a target. An example of such a binding protein, which has an affinity for human serum albumin and may be used as fusion partner with TNF-α binding SPA domain derivative of the invention, is the albumin binding domain of streptococcal protein G (SPG) (Nygren P-Å et al (1988) Mol Recogn 1:69-74; Kraulis P J et al, FEBS Lett 378:190 (1996)). A fusion polypeptide between a TNF-α binding, SPA domain-related polypeptide and the albumin binding domain of SPG thus falls within the scope of the present invention. When the polypeptide according to the invention is administered to a human subject as a therapeutic agent or as a targeting agent, the fusion thereof to a moiety which binds serum albumin may prove beneficial, in that the half-life in vivo of such a fusion protein may likely prove to be prolonged as compared to the half-life of the SPA domain-related TNF-α binding moiety in isolation (this principle has been described e.g. in WO91/01743).

Other possibilities for the creation of fusion polypeptides are also contemplated. Thus, a TNF-α binding SPA domain-related polypeptide according to the first aspect of the invention may be covalently coupled to a second or further moiety or moieties, which in addition to or instead of target binding exhibit other functions. One example is a fusion between one or more TNF-α binding polypeptide(s) and an enzymatically active polypeptide serving as a reporter or effector moiety. Examples of reporter enzymes, which may be coupled to the TNF-α binding polypeptide to form a fusion protein, are known to the skilled person and include enzymes such as galactosidase, alkaline phosphatase, horseradish peroxidase, carboxypeptidase. Other options for the second and further moiety or moieties of a fusion polypeptide according to the invention include, also without limitation, fluorescent polypeptides, such as green fluorescent protein, red fluorescent protein, luciferase and variants thereof.

With regard to the description above of fusion proteins incorporating a TNF-α binding polypeptide according to the invention, it is to be noted that the designation of first, second and further moieties is made for clarity reasons to distinguish between TNF-α binding moiety or moieties on the one hand, and moieties exhibiting other functions on the other hand. These designations are not intended to refer to the actual order of the different domains in the polypeptide chain of the fusion protein. Thus, for example, said first moiety may without restriction appear at the N-terminal end, in the middle, or at the C-terminal end of the fusion protein.

The invention also encompasses polypeptides in which a TNF-α binding polypeptide as described above has been provided with a label group, such as at least one fluorophore, biotin or a radioactive isotope, for example for purposes of detection of the polypeptide.

The five domains of naturally occurring staphylococcal protein A, i.e. the E domain, the D domain, the A domain, the B domain and the C domain are useful starting points for the creation of a polypeptide according to the invention (see for example Uhlén et al, J. Biol. Chem. 259:1695-1702 (1984), reporting the original cloning of SPA).

Another example of an SPA related domain for use as a starting point for the creation of a polypeptide according to the invention is protein Z, derived from domain B of staphylococcal protein A (Nilsson B et al (1987), supra). As pointed out in the Background section, this protein has previously been used as a scaffold structure for the creation of molecules, denoted Affibody® molecules, capable of binding to a variety of targets. The 58 amino acid sequence of unmodified protein Z, denoted Z00000, is set out in SEQ ID NO:1 and illustrated in FIG. 1.

In an embodiment of the polypeptide according to the invention, it is related to a domain of SPA in that the sequence of the polypeptide corresponds to the sequence of the SPA domain having 1 to about 20 substitution mutations. Other embodiments may have 1 to about 13 substitution mutations such as 4 to about 13 substitution mutations.

In a more specific embodiment of the polypeptide according to the invention, its sequence corresponds to the sequence set forth in SEQ ID NO:1 but having 1 to about 20 substitution mutations, such as 4 to about 20, 1 to about 13 or 4 to about 13 substitution mutations.

The polypeptide according to the invention may in some embodiments correspond to the sequence set forth in SEQ ID NO:1, which sequence comprises substitution mutations at one or more of the positions 17, 18, 25, 27, 28 and 32. Additionally, the sequence of the polypeptide according to the invention may comprise substitution mutations at one or more of the positions 13, 14, 24 and 35 of the sequence of SPA protein Z in SEQ ID NO:1. The sequence may furthermore comprise substitution mutations at one or more of the positions 9, 10 and 11 of the sequence of SPA protein Z in SEQ ID NO:1.

For example in a TNF-α binding polypeptide in accordance with the invention which is related to protein Z, the amino acid at position 3 corresponds to the amino acid at position 3 in the original (or "wild-type") sequence of protein Z shown in SEQ ID NO:1 when the TNF-α binding polypeptide has 58 amino acids, but, when the polypeptide has an additional 10 amino acid N terminal extension, the amino acid at position 13 of that polypeptide corresponds to the amino acid at position 3 of the protein Z sequence in SEQ ID NO:1.

The sequence of a polypeptide according to another embodiment of the invention corresponds to SEQ ID NO:1, comprising at least a substitution mutation at a position corresponding to position 32 in SEQ ID NO:1 from glutamine to arginine.

The sequence of a polypeptide according to yet another embodiment of the invention corresponds to SEQ ID NO:1, comprising at least a substitution mutation at a position corresponding to position 18 in SEQ ID NO:1 from histidine to arginine.

The sequence of a polypeptide according to a further embodiment of the invention corresponds to SEQ ID NO:1, comprising at least a substitution mutation at a position corresponding to position 28 in SEQ ID NO:1 from asparagine to an amino acid selected from tyrosine and arginine, more preferably to tyrosine.

The sequence of a polypeptide according to another embodiment of the invention corresponds to SEQ ID NO:1, comprising at least a substitution mutation at a position corresponding to position 27 in SEQ ID NO:1 from arginine to tyrosine.

The sequence of a polypeptide according to another embodiment of the invention corresponds to SEQ ID NO:1, comprising at least a substitution mutation at a position corresponding to position 25 in SEQ ID NO:1 from glutamic acid to an amino acid residue selected from histidine and glutamine, more preferably to histidine.

In another embodiment of the invention, the sequence of the polypeptide corresponds to SEQ ID NO:1, comprising at least a substitution mutation at a position corresponding to position 17 in SEQ ID NO:1 from leucine to an amino acid residue selected from glycine and alanine, more preferably to glycine.

In another embodiment of the invention, the sequence of the polypeptide corresponds to SEQ ID NO:1, comprising at least a substitution mutation at a position corresponding to position 13 in SEQ ID NO:1 from phenylalanine to isoleucine.

Examples of specific sequences of polypeptides according to the invention, each comprising one or more of the specific mutations described above, are set out in SEQ ID NO:2-84 and illustrated in FIG. 1. TNF-α binding characteristics of these polypeptides, and of polypeptides in which these polypeptides are present as TNF-α binding domains, are disclosed in the examples that follow.

Thus, as non limiting examples of the TNF-α binding polypeptides of the invention, the invention encompasses any TNF-α binding polypeptide, or any TNF-α binding domain, whose amino acid sequence fulfils one definition selected from the following:
   a) it is selected from SEQ ID NO:2-84;
   b) it is an amino acid sequence having 85% or greater identity to a sequence selected from SEQ ID NO:2-84;

As evident from this definition, in addition to a polypeptide whose amino acid sequence is selected from SEQ ID NO:2-84, the present invention also encompasses variants thereof. The amino acid sequences of such encompassed variants exhibit small differences only in comparison with SEQ ID NO:2-84. One definition of such variants is given in b) above, i e a TNF-α binding polypeptide with an amino acid sequence having at least 85% identity to a sequence selected from SEQ ID NO:2-84. In some embodiments of the invention, the amino acid sequence has at least 90% identity, at least 95% identity, or at least 98% identity to a sequence selected from SEQ ID NO:2-84.

As discussed above, the polypeptide according to the invention may be present as a moiety or domain in a fusion protein, or be provided with a tag of additional amino acid residues. In the experimental section of the present disclosure, the TNF-α binding properties of several such constructs are tested. The polypeptides described are all included in the scope of the present invention.

As an alternative to using an unmodified SPA domain as a starting point, the SPA domain may also be subjected to mutagenesis in order to increase the stability thereof in alkaline conditions. Such stabilization involves the site-directed substitution of any asparagine residues appearing in the unmodified sequence with amino acid residues that are less sensitive to alkaline conditions. When using the polypeptide according to the invention as an affinity ligand in affinity chromatography, this property of having a reduced sensitivity to alkali provides benefits; affinity chromatography columns are frequently subjected to harsh alkali treatment for cleaning in place (CIP) between separation runs, and the ability to withstand such treatment prolongs the useful lifetime of the affinity chromatography matrix. As an example, making use of protein Z as starting point, the polypeptide according to the invention may, in addition to the substitution mutations conferring TNF-α binding, have modifications in that at least one asparagine residue selected from N3, N6, N11, N21, N23, N28, N43 and N52 has been substituted with an amino acid residue that is less sensitive to alkaline treatment. Non-limiting examples of such polypeptides are those having the following sets of mutations (with respect to SEQ ID NO:1): N3A; N6D; N3A, N6D and N23T; N3A, N6D, N23T and N28A; N23T; N23T and N43E; N28A; N6A; N11S; N11S and N23T; N6A and N23T. Thus, these SPA domains, as well as other SPA domains that have been subjected to asparagine mutation for stability reasons, may all be subjected to further substitution mutation of amino acid residues in order to obtain a TNF-α binding polypeptide of the invention. Alternatively, a TNF-α binding polypeptide of the invention which comprises asparagine residues may be subjected to further mutation to replace such residues. Evidently, this latter alternative is only possible to the extent that TNF-α binding capability of such a molecule is retained.

The invention also encompasses polypeptides that have been derived from any of the polypeptides described above through the generation of a fragment of the above polypeptides, which fragment retains TNF-α affinity. The fragment polypeptide is such that it remains stable, and retains the specificity to bind TNF-α. Braisted A C and Wells J A in Proc Natl Acad Sci USA 93:5688-5692 (1996) show that it is possible to create fragments of a wild-type SPA domain with retained binding specificity to immunoglobulin G. By using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning with the polypeptides according to the first aspect of the invention, the skilled man would be able to obtain a "minimized" TNF-α binding polypeptide with the same binding properties as that of the "parent" TNF-α binding polypeptide. Hence, a polypeptide constituting a fragment of a polypeptide according to the above aspect of the invention, which fragment retains binding affinity for TNF-α, is a further aspect of the invention.

Another aspect of the present invention relates to a nucleic acid molecule comprising a sequence which encodes a polypeptide according to the invention.

A further aspect of the present invention relates to an expression vector comprising the nucleic acid molecule of the previous aspect, and other nucleic acid elements that enable production of the polypeptide according to the invention through expression of the nucleic acid molecule.

Yet another aspect of the present invention relates to a host cell comprising the expression vector of the previous aspect.

The latter three aspects of the invention are tools for the production of a polypeptide according to the invention, and the skilled person will be able to obtain them and put them into practical use without undue burden, given the information herein concerning the polypeptide that is to be expressed and given the current level of skill in the art of recombinant expression of proteins. As an example, a plasmid for the expression of unmodified protein Z (see e g Nilsson B et al (1987), supra) may be used as starting material. The desired substitution mutations may be introduced into this plasmid, using known techniques, to obtain an expression vector in accordance with the invention.

However, the polypeptide according to the invention may also be produced by other known means, including chemical synthesis or expression in different prokaryotic or eukaryotic hosts, including plants and transgenic animals. When using chemical polypeptide synthesis, any of the naturally occurring amino acid residues in the polypeptide as described above may be replaced with any corresponding, non-naturally occurring amino acid residue or derivative thereof, to the extent that the TNF-α binding capacity of the polypeptide is not substantially affected. Such non-classical amino acids, or synthetic amino acid analogs, include, but are not limited to, the D-isomers of the common amino acids, α-amino isobutyric acid, 4-amino butyric acid, 2-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoroamino acids, designer amino acids such as β-methyl amino acids, Cα-methyl amino acids, Nα-methyl amino acids, and amino acid analogs in general. Furthermore, the amino acid residues can be present in D or L form.

The present invention also concerns different aspects of using the above-described TNF-α binding polypeptide, as well as various methods for treatment, diagnosis and detection in which the polypeptide is useful due to its binding characteristics. When referring to the "TNF-α binding polypeptide" in the following description of these uses and methods, this term is intended to encompass the TNF-α binding polypeptide alone, but also all those molecules based on this polypeptide described above that e g constitute fragments thereof and/or incorporate the TNF-α binding polypeptide as a moiety in a fusion protein and/or are conjugated to a label or therapeutic agent and/or are provided with additional amino acid residues as a tag or for other purposes. As explained above, such fusion proteins, derivatives, fragments etc form a part of the present invention.

According to another aspect of the present invention, a method of separation, removal and/or purification of TNF-α is provided. The method comprises a step of affinity separation, in which step a polypeptide according to the first aspect of the invention is used. Thus, the invention provides the use of the polypeptide as described above in a method of affinity separation. Suitably, the method involves a separation device, such as chosen among chromatographic media, membranes, cellulose, silica, agarose, polyacrylamide, magnetic beads, two-phase systems and other such materials commonly used in separation. For example, a suitable solid matrix may include a surface support made from polystyrene, acrylamide, etc., or polymeric plastic, polymeric plastic beads ranging in sizes 0.1 to 2 mm.

In an embodiment, the polypeptide according to the invention is coupled to the separation device. The thus obtained separation device, having polypeptide according to the invention coupled thereto, is referred to as an affinity matrix.

For the purposes of purification of TNF-α from a sample, the sample containing TNF-α to be purified is suitably applied to such an affinity matrix under conditions that are conducive to binding of TNF-α to the matrix. Thereafter, the affinity matrix is washed under conditions such that the binding of TNF-α to the matrix is maintained, but most, ideally all, other proteins and contaminants bound to the matrix are washed away. In an elution step, the matrix is treated such that TNF-α is released from the matrix in TNF-α enriched fraction denoted "TNF-α fraction", which may be recovered.

If, conversely, the purpose of the separation is the removal of TNF-α, essentially the same steps as above are suitably followed, with some exceptions. The sample containing TNF-α to be removed is suitably applied to an affinity matrix under conditions that are conducive to binding of TNF-α to the matrix. Thereafter, the affinity matrix is washed under conditions such that the binding of TNF-α to the matrix is maintained, but most, ideally all, other proteins are recovered in the flow-through, thus obtaining a "depleted fraction" with a substantial reduction in TNF-α content, which is recovered. Thus, the non-TNF-α constituents of the sample, that were discarded in the purification method above, may instead be retained and used and/or processed further.

Another method of the invention, also performed with the purpose of removing TNF-α from a sample but with the added requirement that the "depleted fraction" should not contain any substances or solvents not present in the original sample, comprises a similar sequence of steps. The sample containing TNF-α to be removed is brought to interact with the affinity matrix under conditions that are conducive to binding of TNF-α to the matrix, and subsequently recovered. This yields a sample ("depleted fraction") with a substantial reduction in TNF-α content, which furthermore is essentially free from anything that was not present in the sample before application thereof to the affinity matrix.

As a further alternative of the inventive method, both the "depleted fraction" and the "TNF-α fraction" may be recovered from the same separation run. Then, once again, the sample containing TNF-α is suitably applied to an affinity matrix under conditions that are conducive to binding of TNF-α to the matrix. Thereafter, the affinity matrix is washed, under conditions such that the binding of TNF-α to the matrix is maintained, but most, ideally all, other proteins are recovered in the flow-through. The thus obtained "depleted fraction" with a substantial reduction in TNF-α content is recovered. In an elution step, the matrix is treated such that TNF-α is released from the matrix in TNF-α enriched fraction denoted "TNF-α fraction", which is recovered.

Another related aspect of the invention is a method for reducing the content of TNF-α in a portion of a body fluid of a human, comprising the steps to: a) provide a portion of a body fluid from a human; b) apply the portion to an affinity matrix comprising a TNF-α binding polypeptide as described herein, under conditions enabling binding of the TNF-α to the affinity matrix, thereby causing a reduction of the content of TNF-α in the portion of body fluid; and optionally c) return at least a part of said portion of body fluid to said human.

The method according to this aspect of the invention may be directed to reducing the content of TNF-α in a body fluid of a subject suffering from complications arising from the presence of TNF-α, whereby the symptoms are alleviated by performing the method. Alternatively, the method may be directed to reducing the content of TNF-α in a body fluid aliquot which is intended for use as a supply in a transfusion to another person than the one from whom the sample of body fluid originates. The body fluid may for example be whole blood, plasma or serum. Hence, by using the method according to the invention, subjects suffering from complications arising from the presence of TNF-α could be treated by extracorporeal removal of TNF-α. For example, the levels of proinflammatory molecules such as TNF-α increase dramatically in patients undergoing surgery, and it has been shown that these elevated levels are most likely a combined effect of anesthesia, surgical trauma and endothelial lesions. Due to the negative effect of the proinflammatory molecules on the clinical outcome of surgical patients, it would be beneficial to provide a therapeutic inhibition of the effect of pro-inflammatory molecules. According to this aspect of the invention, this is achieved directly by the decrease in TNF-α levels in the body fluid upon carrying out of the inventive method. In other words, this is an example of an extracorporeal therapy which allows specific elimination of TNF-α in body fluids to be returned to, or transfused to, surgical patients. The skilled person with experience in the art of extracorporeal devices, e g for immunoadsorption, could use this method with the inventive affinity matrix for treatment of a subject, by extracorporeal removal of TNF-α from for example a sample of blood from said subject or for example an aliquot of blood to be transfused to said subject. Affinity adsorption treatment of humans is described in many previous publications, inter alia in U.S. Pat. No. 5,753,227, U.S. Pat. No. 6,264,623 and U.S. Pat. No. 6,676,622, all to Strahilevitz M.

In a further aspect, the invention is directed to an affinity matrix comprising a TNF-α binding polypeptide according to the invention as described above.

Yet another aspect of the present invention is constituted by the use of a TNF-α binding polypeptide as described herein in a method for detecting TNF-α in a biological fluid sample. This method comprises the steps of (i) providing a biological fluid sample from a patient to be tested, for example a blood plasma sample for the measurement of plasma TNF-α levels, (ii) applying a TNF-α binding polypeptide as described herein to the sample under conditions such that binding of the polypeptide to any TNF-α present in the sample is enabled, (iii) removing non-bound polypeptide, and (iv) detecting bound polypeptide. The amount of the detected bound polypeptide is correlated to the amount of TNF-α present in the sample. In step (ii), the application of a TNF-α binding polypeptide to the sample may be performed in any suitable format, and includes for example the situation when a TNF-α binding polypeptide is immobilized on a solid support with which the sample is brought into contact, as well as set-ups in which a TNF-α binding polypeptide is present in solution. The method according to this aspect of the invention may suitably be performed in a standard 96-well format, in analogy to existing ELISA tests. As a preferred alternative, the polypeptide according to the invention is used as one or more reagent(s) in a sandwich assay, whereas a monoclonal or polyclonal antibody directed against TNF-α may be used as other reagents. A sandwich assay using the SPA domain derived TNF-α binding molecule as either capture or detection agent shows several advantages compared to using conventional antibody reagents for both capture and detection. One specific such advantage is the elimination of false positive results in the absence of TNF-α, which false positives are due to cross-linking between capture and detection anti-bodies by for example heterophilic anti-animal Ig anti-bodies (HAIA).

As an additional aspect, the invention provides the use of a TNF-α binding polypeptide as described herein in a method of detection of TNF-α in tissue samples. This method comprises the steps of (i) providing a tissue sample suspected of containing TNF-α, (ii) applying a TNF-α binding polypeptide according to the invention to said sample under conditions conducive for binding of the polypeptide to any TNF-α present in the sample, (iii) removing non-bound polypeptide, and (iv) detecting bound polypeptide. The amount of the detected bound polypeptide is correlated to the amount of TNF-α present in the sample.

BRIEF DESCRIPTION OF THE DRAWINGS

FIG. 1 shows an alignment of the sequences of the sequence listing. The amino acid positions that have been subjected to modification in the examples of TNF-α binding polypeptides according to the invention (SEQ ID NO:2-84) are indicated in bold face.

Figure 2:
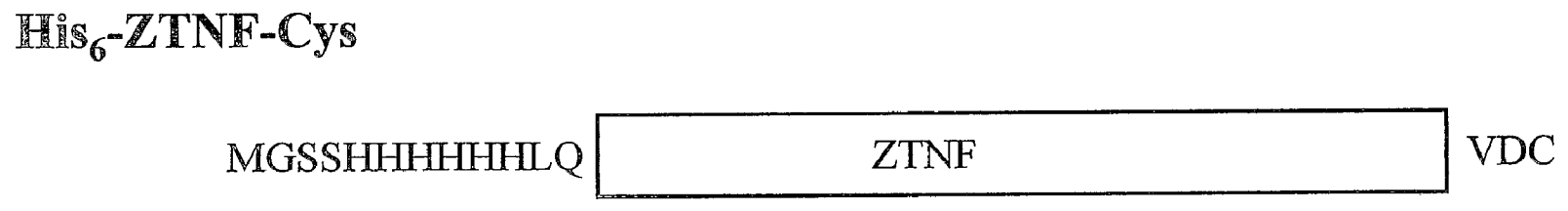

FIG. 2 is a schematic illustration of the amino acid sequence of the polypeptides according to the invention expressed and characterized in Example 2. ZTNF represents a TNF-α binding domain with a sequence selected from the sequences of Z00183, Z00185, Z00192, Z00194, Z00198, Z00200, Z00203, Z00205, Z00207, Z00209, Z00210 and Z00211.

FIG. 4 is a schematic illustration of the amino acid sequence of the polypeptides according to the invention expressed and characterized in Example 3. A: $His_6$-$(Z00734)_4$; B: $His_6$-$(Z00752)_4$; C: $His_6$-$(Z00771)_4$.

Figure 3A:
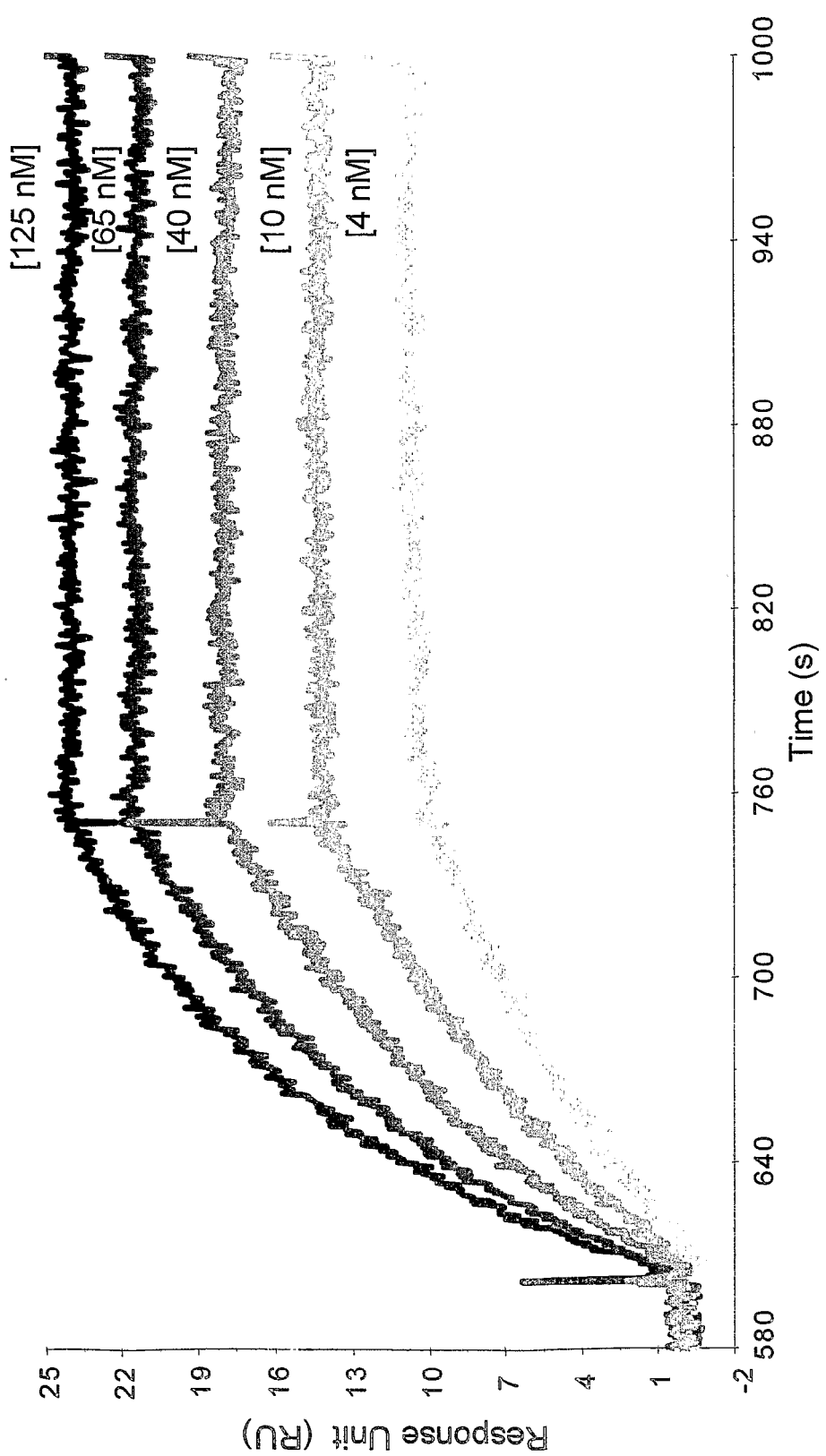
FIG. 3 shows Biacore® sensorgrams obtained after duplicated injections of different concentrations of TNF-α over sensor chip surfaces having the following ZTNF variant immobilized thereto. A: $His_6$-Z00185; B: $His_6$-Z00192; C: $His_6$-Z00198; D: $His_6$-Z00210. The concentration of TNF-α used in each binding curve of the four sensorgrams has been indicated in the figure.
Figure 3B:
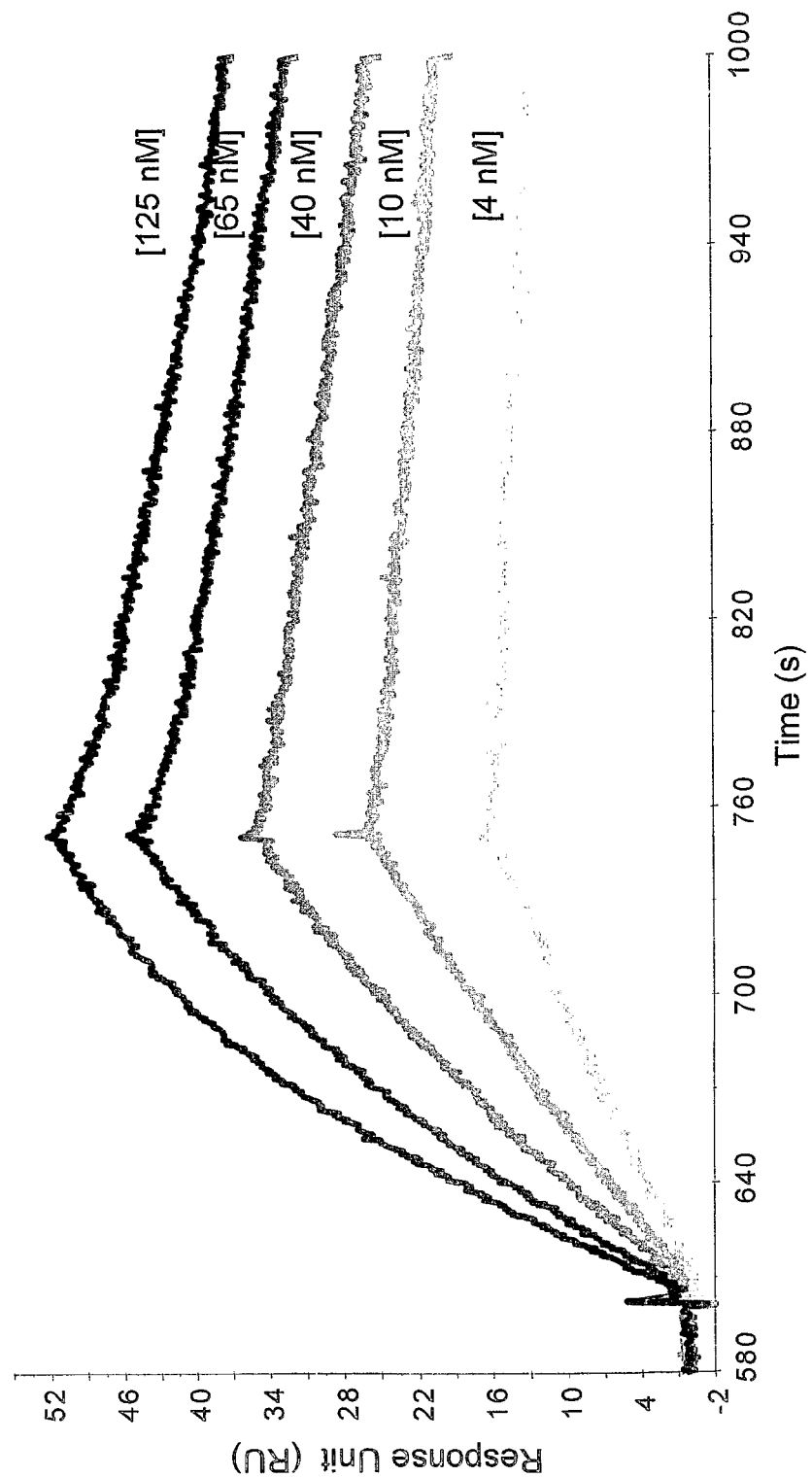
Figure 3C:
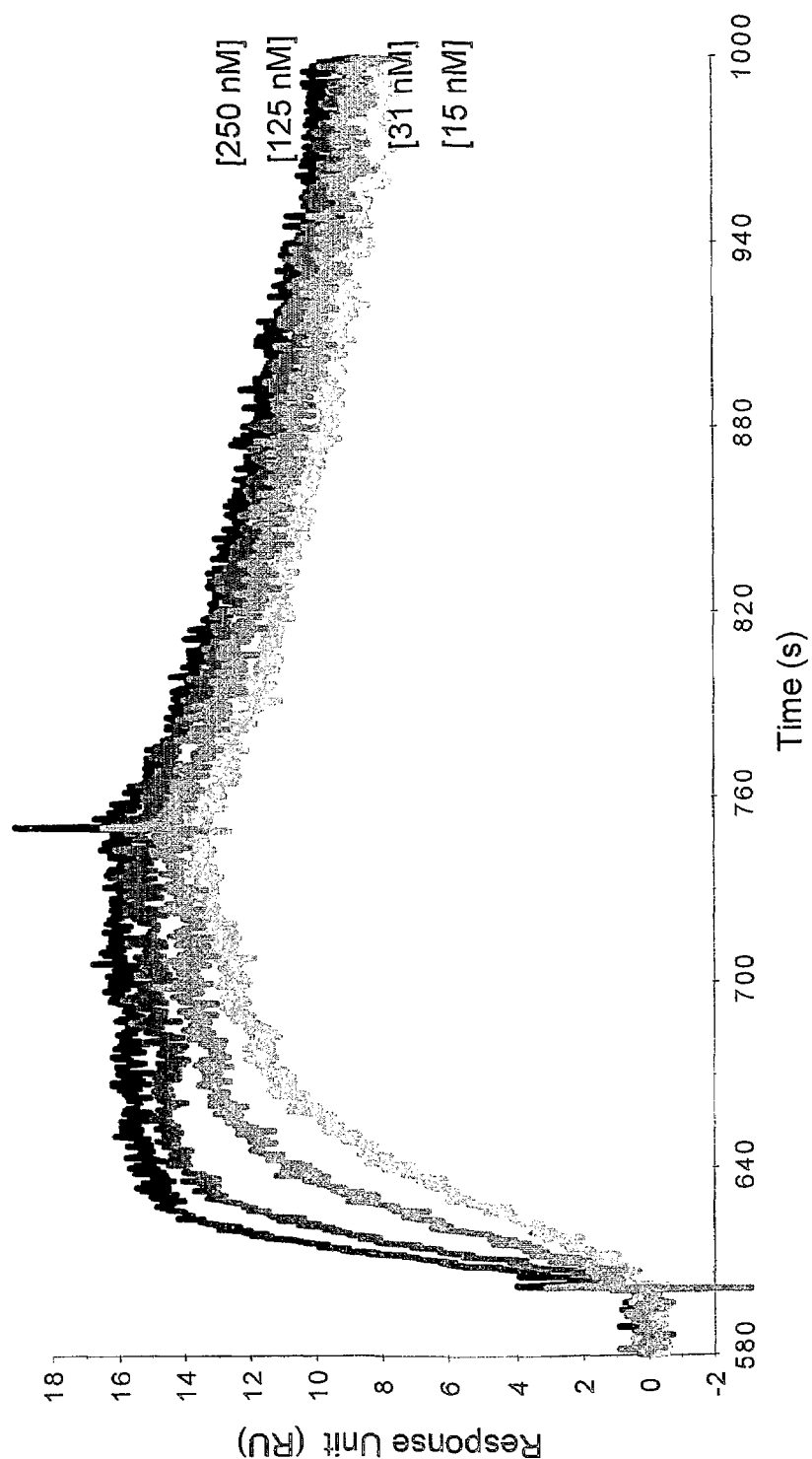
Figure 3D:
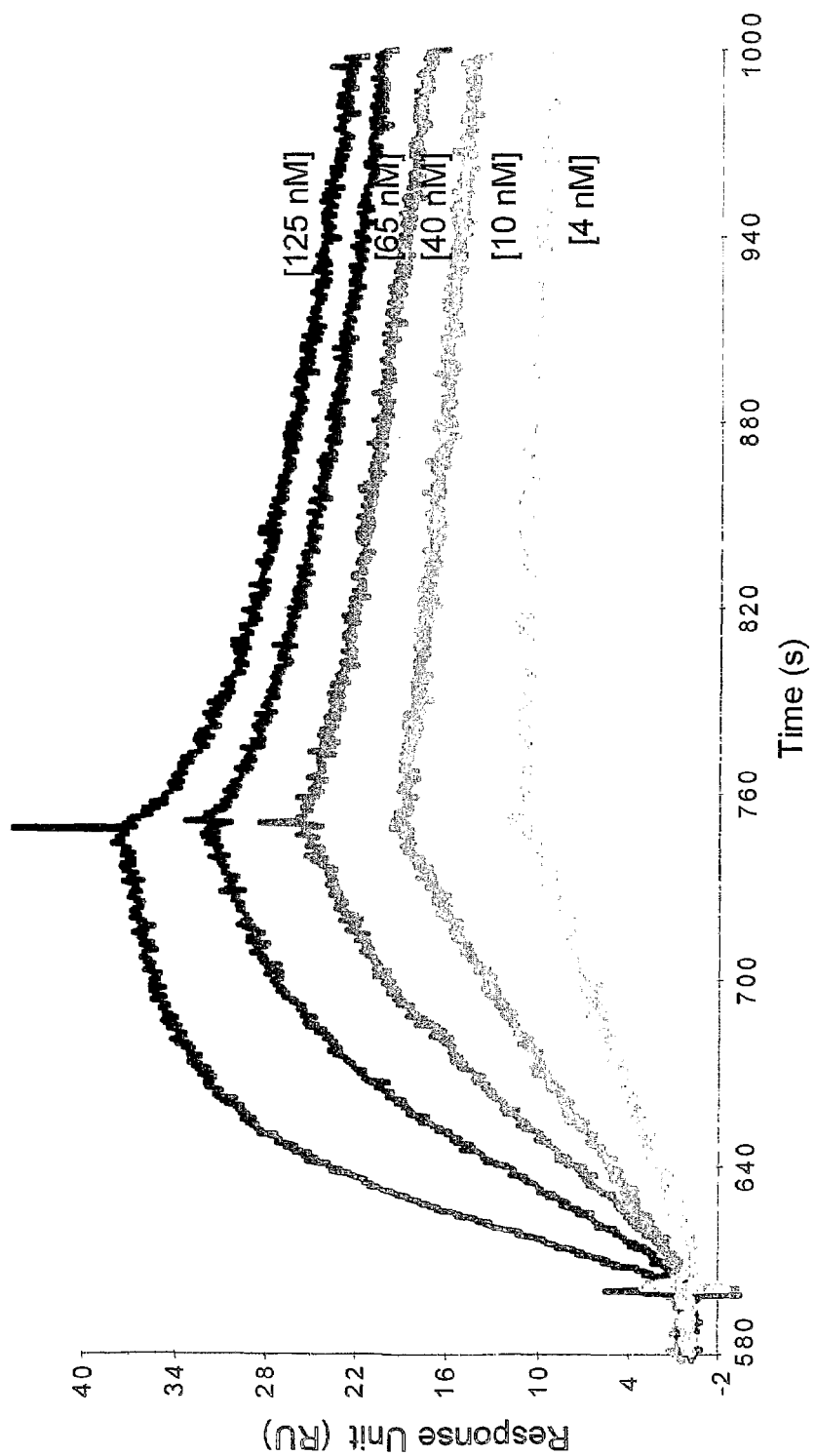

The invention will now be illustrated further through the non-limiting description of experiments conducted in accordance therewith. In these experiments, several TNF-α binding polypeptides according to the invention were selected from a library of a multitude of different SPA domain related polypeptides, and subsequently characterized.

Unless otherwise specified, conventional molecular biology methods were used throughout.

TNF-α binding variants of protein Z ("Z variants") are sometimes collectively denoted ZTNF.

EXAMPLE 1

Selection and ELISA Study of TNF-α Binding Polypeptides

Library Panning and Clone Selection

A combinatorial phage display library was prepared essentially as described in Nord K et al (1995, supra). The pool of this library which was used in the present study comprised $3.3 \times 10^9$ variants of protein Z (Affibody® molecules), with random amino acid residues at positions 9, 10, 11, 13, 14, 17, 18, 24, 25, 27, 28, 32 and 35. TNF-α binding Z variants were selected using biotin-conjugated, recombinant TNF-α produced in E. coli as target (Research Diagnostics Inc, cat no RDI-301X; delivered as a lyophilizate from 3 mM Tris solution, pH 8.0, with no additives; SEQ ID NO:85). After four cycles of selection, clones were picked for phage Enzyme Linked ImmunoSorbent Assay (ELISA) in order to perform an analysis of their TNF-α binding activity.

Elisa for Analysis of TNF-α Binding

Z variants from clones obtained after four rounds of selection were expressed in 96 well plates and screened for TNF-α binding activity using ELISA. The expressed products were fusion proteins between prospective TNF-α binding Z variants and an albumin binding domain (ABD) of streptococcal protein G. Single colonies were inoculated in 1 ml TSB+YE medium (tryptic soy broth with yeast extract) supplemented with 100 µg/ml ampicillin and 1 mM IPTG (isopropyl β-D-1-thiogalactopyranoside) in deep well plates and grown over night at 37° C. Cells were pelleted by centrifugation at 3000 g for 15 min, resuspended in 400 µl PBS-T (PBS with 0.1% Tween-20; PBS: 2.68 mM KCl, 1.47 mM $KH_2PO_4$, 137 mM NaCl, 8.1 $Na_2HPO_4$, pH 7.4) and frozen at −80° C. Frozen samples were thawed in a water bath and cell debris was pelleted at 3700 g for 40 min, Supernatants containing fusion proteins between prospective TNF-α binding Z variants and ABD were collected and stored at 4° C. until use in ELISA according to the following.

Microtitre wells (Costar, cat no 9018) were coated overnight at 4° C. with 100 µl human serum albumin (HSA; Sigma, cat no A-3782) at a concentration of 6 µg/ml in ELISA coating buffer (0.1 M sodium carbonate; Merck). The wells were blocked with blocking buffer (0.5% casein in PBS) for 2 h at room temperature. 100 µl of each prepared fusion protein solution were added, and plates were incubated for 1.5 hours at room temperature. Biotinylated TNF-α at a concentration of 1 µg/ml in PBS-T was added to the wells and incubated for 1.5 h. Bound TNF-α was detected either with streptavidin conjugated to horseradish peroxidase (SA-HRP; Dako, cat no P0397) or with streptavidin conjugated to poly-horse radish peroxidase (SA-polyHRP40; Research Diagnostics, cat no RDI-PHRP40-SA2), each diluted 1:5000 in PBS-T, and incubated for 1 hour at room temperature. Developing solution was prepared by mixing an equal volume of TMB substrate A and B according to the manufacturer's instructions (ImmunoPure TMB Substrate Kit; Pierce cat no 34021). 100 µl were added to each well. After 30 min of incubation in darkness, 100 µl stop solution (2 M $H_2SO_4$) was added. The plates were read at $A_{450}$ in an ELISA spectrophotometer (Basic Sunrise; Tecan).

In experiments using SA-HRP for detection, TNF-α binders were identified using a threshold criterion of an $A_{405}$ above 0.17. In experiments using SA-polyHRP40, the threshold value was set to an $A_{405}$ above 0.5. The Z variant fusion proteins giving a signal above the threshold value in the ELISA experiments were selected for DNA sequence analysis.

DNA Sequence Analysis

PCR fragments were amplified from the colonies obtained after four rounds of selections using oligonucleotides AFFI-21 (SEQ ID NO:86) and AFFI-22 (SEQ ID NO:87). Amplified fragments were sequenced using the biotinylated oligonucleotide AFFI-72 (SEQ ID NO:88) and the ABI PRISM dGTP, BigDye™ Terminator v3.0 Ready Reaction Cycle Sequencing Kit (Applied Biosystems) according to the manufacturer's recommendations. The sequencing reactions were purified by binding to magnetic streptavidin-coated beads using a Magnatrix 8000, and analyzed on an ABI PRISM® 3100 Genetic Analyser (Applied Biosystems). The sequence analysis resulted in 74 unique sequences. The sequences of the Z variants expressed by the clones chosen based on the ELISA binding assay are given in FIG. 1, and identified in the sequence listing as SEQ ID NO:2-75.

EXAMPLE 2

Expression and Characterization of TNF a Binding Polypeptides

TNF-α binding variants were selected for further characterization on the basis of i) ELISA values obtained as described in Example 1, ii) results from clustering of amino acid sequences and iii) the abundance of the sequence in the selection result. TNF-α binding variants with the amino acid cysteine in any variable positions were eliminated. The chosen clones were Z00183, Z00185, Z00192, Z00194, Z00198, Z00200, Z00203, Z00205, Z00207, Z00209, Z00210 and Z00211 (see FIG. 1). All experiments of this Example were individually conducted with all of these variants. The TNF-α binding Z variants were produced in small scale as $His_6$-fusion proteins with an additional C-terminal cysteine residue. Purified proteins were affinity screened for TNF-α binding activity using surface plasmon resonance technology (SPR).

Expression and Purification of Fusion Polypeptides

Fusion polypeptides were expressed in E. coli BL21(DE3) cells, by adapting the methods of Nilsson B et al, Eur. J. Biochem. 224 (1994), 103-108 and using conventional molecular biology methods for cloning. The expression vector used encodes a fusion polypeptide as schematically illustrated in FIG. 2, in which ZTNF represents the different TNF-α binding domains with the sequences of Z00183, Z00185, Z00192, Z00194, Z00198, Z00200, Z00203, Z00205, Z00207, Z00209, Z00210 and Z00211 (see FIG. 1). One additional variant, denoted Z00468, was obtained due to contamination of the original Z00209 preparation. We could not exclude that Z00468 was a more interesting clone than Z00209, so this clone was included in the study.

A colony of each Z variant transformed into E. coli BL21 (DE3) was used to inoculate 10 ml TSB (3% w/v tryptic soy broth) medium supplemented with 50 µg/ml kanamycin. The cultures were grown over night at 37° C. The following day, 20 µl of each overnight culture was used to inoculate 5 ml TSB+YE (3% w/v tryptic soy broth+0.5% w/v yeast extract) medium supplemented with 50 µg/ml kanamycin in a 24 well plate (2 wells/variant). The cultures were grown at 150 rpm at 37° C. to an $OD_{600}$ of −0.7-1, which was followed by addition of IPTG (1 M isopropyl-β-D-thiogalactopyranoside) to a final concentration of 0.5 mM and incubation at room temperature over night. Cultures were harvested by centrifugation at 1000 g for 10 minutes and pellets were stored at −80° C. until protein preparation.

The $His_6$-tagged proteins were IMAC purified under denatured conditions using QIAfilter 96 Plates Ni-NTA Superflow kit and QIAsoft 4.1, medium scale protein/Ni-NTA Superflow 96 denat program on a Biorobot 3000 (Qiagen) according to the manufacturer's instructions. Buffer exchange to PBS (2.68 mM KCl, 1.47 mM KH$_2$PO$_4$, 137 mM NaCl, 8.1 Na$_2$HPO$_4$, pH 7.4) with NAP-5 columns (Amersham Biosciences) was performed according to manufacturer's recommendations after the purification.

Protein concentration was determined using the BCA Protein Assay Reagent Kit (Pierce, cat no 23225) as recommended by the manufacturer. The purity of the proteins was analyzed by SDS-PAGE on 20% polyacrylamide gels under reducing conditions and stained with Coomassie Blue R, using the Phast™ system (Amersham Biosciences) according to the manufacturer's recommendations. All protein preparations exhibited a high degree of purity.

Biosensor Screening of Expressed Z Variants

Biacore analyses were performed with the Z variants, TNF-α, HSA or IgG immobilized on the surface of sensor chips in a Biacore® 2000 instrument (Biacore AB).

HSA, IgG and TNF-α were immobilized in different flow cells by amine coupling onto the carboxylated dextran layer on surfaces of CM-5 chips (research grade; Biacore AB), according to the manufacturer's recommendations. The first cell surface (FC-1) on the chip was activated and deactivated and used as a reference cell during injections. Immobilization resulted in approximately 2400 resonance units for each of the three proteins. Samples of Z variants were diluted in HBS-EP (10 mM HEPES, 150 mM NaCl, 3 mM EDTA, 0.005% P-20, pH 7.4) to a final concentration of 8 µM and injected at a constant flow-rate of 10 µl/minute for 10 minutes, followed by injection of HBS-EP for 5 minutes. The surfaces were regenerated with 2 injections of 50 mM NaOH. All Z variant molecules tested bound to TNF-α. However, it was difficult to interpret the binding activity between different TNF-α binding Z variant. A different immobilization approach was therefore also utilized.

Purified Z variants were immobilized onto the carboxylated dextran layer on surfaces of a CM-5 chip in different flow cells using the ligand thiol method according to the manufacturer's recommendations. One flow cell surface on each chip was activated and deactivated and used as blank during injections. The analytes (TNF-α, HSA and IgG) were diluted in HBS-EP to a final concentration of 30 µg/ml (TNF-α) or 60 µg/ml (HSA and IgG) and injected at a constant flow-rate of 10 µl/minute for 20 minutes followed by 5 minutes injection of HBS-EP. The surface was regenerated with 2 injections of 10 mM HCl. The experiment was repeated using the same Biacore program as described above except that the injection time was changed from 20 to 4 minutes. All variants were found to bind to TNF-α. Moreover, variants Z00185, Z00192, Z00198, Z00210, Z00211 and Z00468 were found to bind specifically to TNF-α. Considering the binding activity and binding specificity of the studied TNF-α binding polypeptides, Z00185, Z00192, Z00198 and Z00210 were chosen for further studies.

Measurement of Apparent K$_D$ Values Using SPR

Biosensor analyses were used to determine kinetic values for Z00185, Z00192, Z00198 and Z00210. The ZTNF molecules were immobilized on the sensor chip surface as described above. TNF-α samples with different concentrations were injected at a flow rate of 60 µl/min. Four or five different concentrations ranging from 4 nM to 250 nM of TNF-α in HBS-EP were measured in duplicate. Dependent on the ZTNF variant that was analyzed, the highest concentration of TNF-α was either 100 or 250 nM. TNF-α was injected randomly as duplicates over the surfaces with thiol coupled ZTNF variants for 2.5 minutes, which was followed by injection of HBS-EP for 10 minutes. The surfaces were subsequently regenerated with 2 injections of 10 mM HCl. The response measured in a reference cell was subtracted from the responses measured in the cells containing immobilized ZTNF polypeptides. FIG. 3A-3D shows sensorgrams obtained from the measurements of Z00185 (3A), Z00192 (3B), Z00198 (3C) and Z00210 (3D). The concentrations of TNF-α used in each binding curve of the four sensorgrams are indicated. Apparent affinity constant (K$_D$) values were calculated using BIAevaluation 3.2 software (Biacore AB), assuming a 1:1 Langmuir binding model. The results are presented in Table 1.

TABLE 1

| Protein | K$_D$ (nM) |
| --- | --- |
| His$_6$-Z00185-Cys | 0.1-0.5 |
| His$_6$-Z00192-Cys | 10-20 |
| His$_6$-Z00198-Cys | 20-30 |
| His$_6$-Z00210-Cys | 2-5 |

EXAMPLE 3

Expression and Characterization of Multimeric Forms of TNF-α Binding Polypeptides Additional selected TNF-α binding variants Z00734, Z00752 and Z00771 (see FIG. 1) were also further characterized. In the experiments of this Example, these polypeptides are sometimes collectively denoted ZTNF. All experiments were individually conducted with all of these variants. The TNF-α binding Z variants were produced as His$_6$-tagged multimers. Affinity of purified proteins for TNF-α was measured using surface plasmon resonance technology (SPR).

Expression and Purification of Fusion Polypeptides

Fusion polypeptides were expressed in *E. coli* BL21(DE3) cells, by adapting the methods of Nilsson B et al, Eur J Biochem 224 (1994), 103-108 and using conventional molecular biology methods for cloning. The expression vector used encoded multimeric forms of ZTNF polypeptides, as schematically illustrated in FIG. 4.

Expression was performed as described in Example 2 above. Proteins were purified from 1 liter cultures of transformants carrying plasmid encoding the proteins His$_6$-(Z00734)$_4$, His$_6$-(Z00752)$_4$ and His$_6$-(Z00771)$_4$. Purification was performed using IMAC with Ni-NTA Superflow columns on the Biorobot 3000 (Qiagen). Total amounts of IMAC purified proteins were determined with the BCA method. The proteins were analyzed by SDS-PAGE on 4-12% polyacrylamide gels and showed good purity.

Biosensor Analysis

Figure 5A:
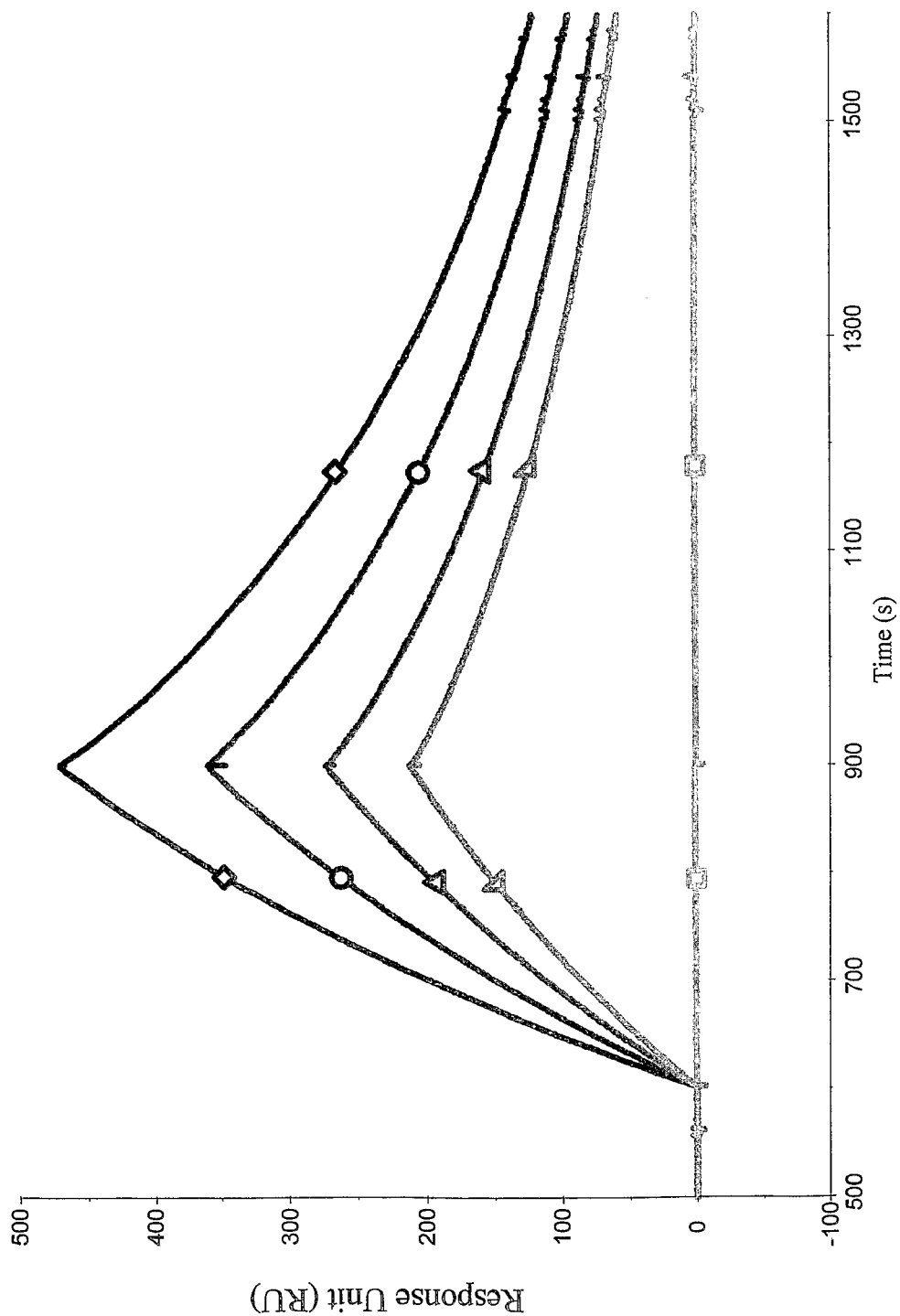
FIG. 5 shows Biacore® sensorgrams obtained after duplicated injections of different concentrations of TNF-α over sensor chip surfaces having the following ZTNF variant immobilized thereto. A: $His_6$-$(Z00734)_4$; B: $His_6$-$(Z00752)_4$; C: $His_6$-$(Z00771)_4$. The concentration of TNF-α used in each binding curve is indicated as follows: 0 μM □, 0.25 μM ▶, 0.5 μM △, 1 μM ○, 2 μM ◇.
Figure 5B:
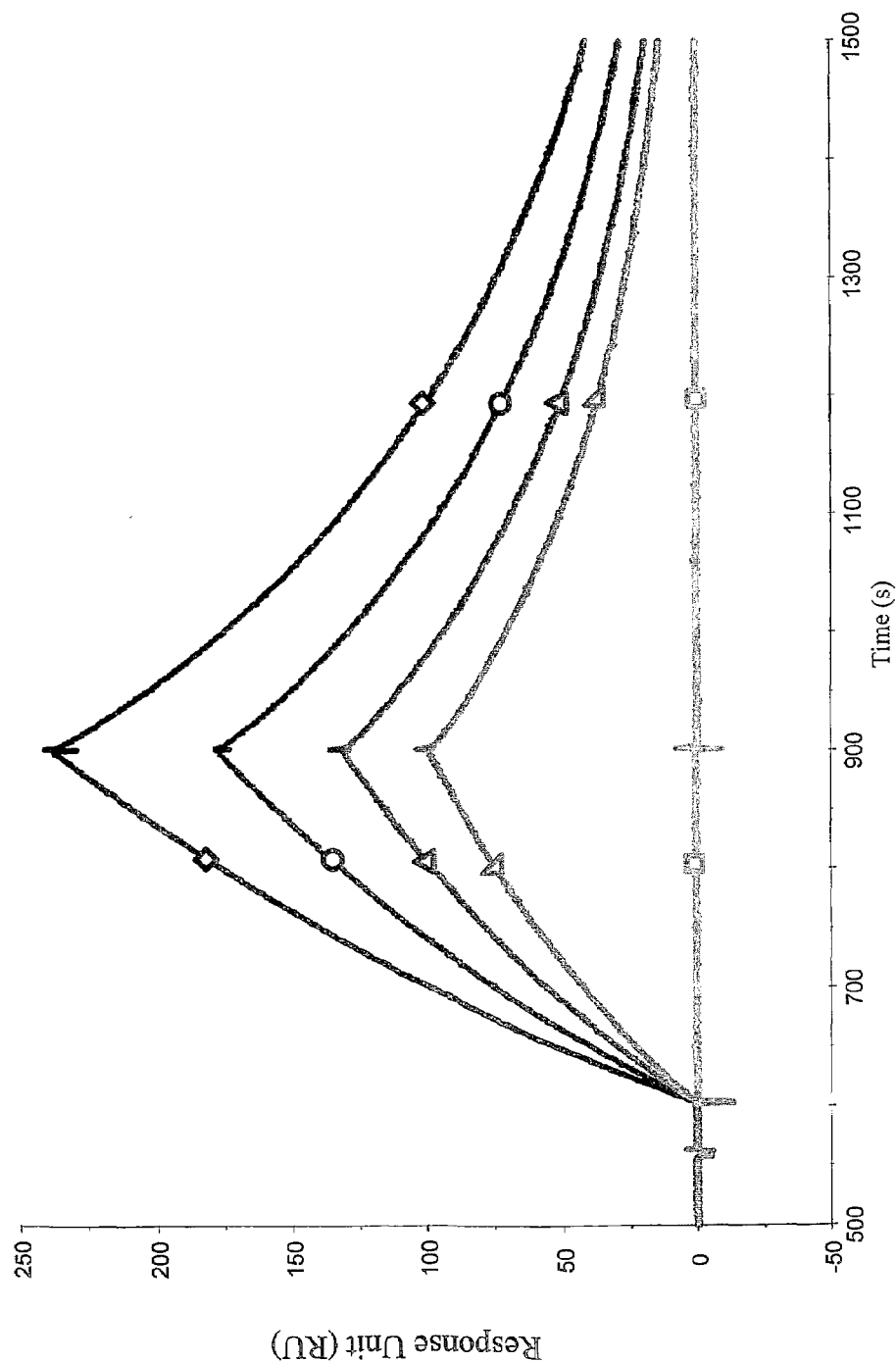
Figure 5C:
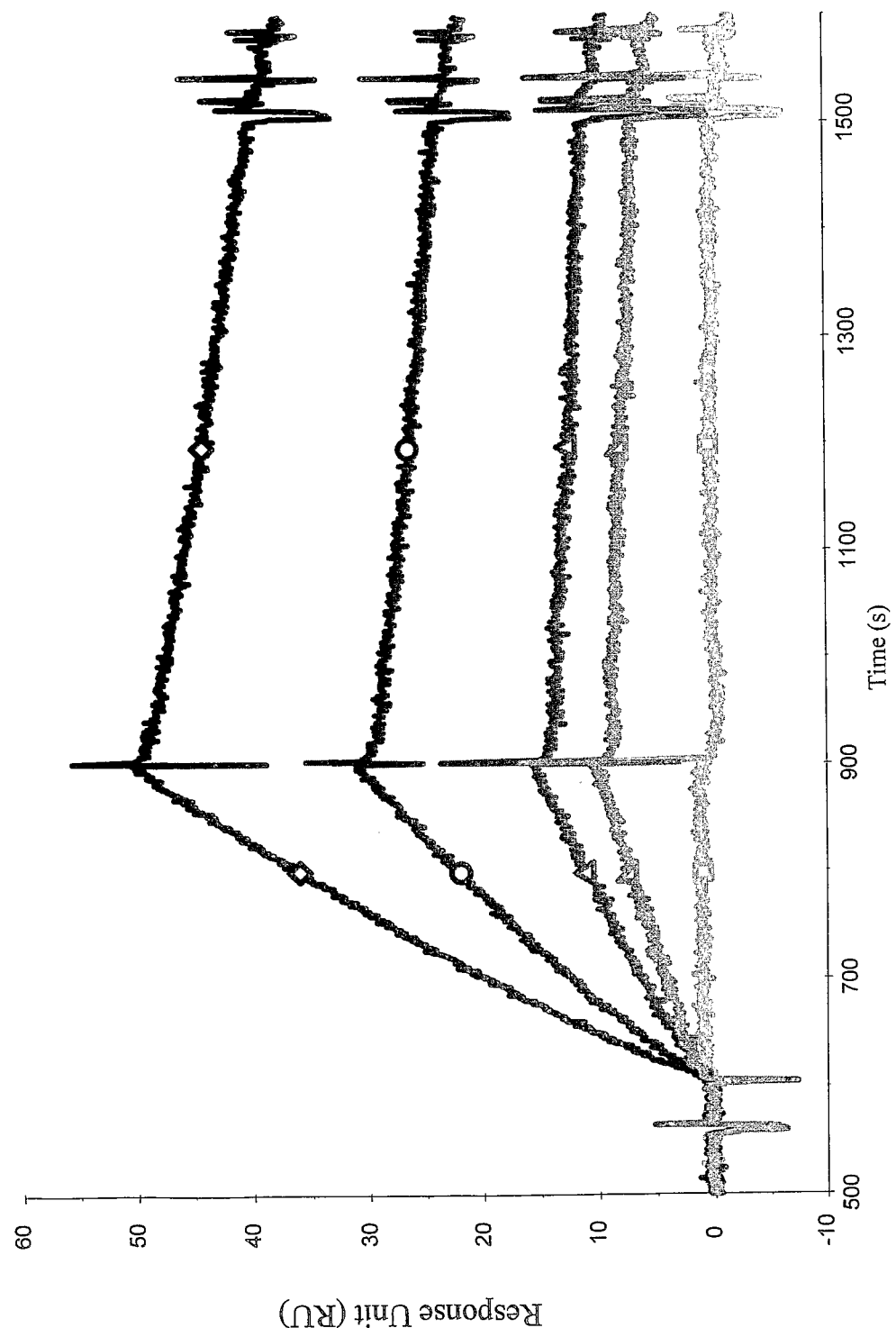

The binding affinity between each of the three multimeric ZTNF variants and TNF-α were analyzed using surface plasmon resonance on a Biacore® 2000 instrument (Biacore AB). The ZTNF variants His$_6$-(Z00734)$_4$, His$_6$-(Z00752)$_4$ and His$_6$-(Z00771)$_4$ were immobilized on the surface using amine coupling onto the carboxylated dextran layer on surfaces of CM-5 chips (research grade; Biacore AB), according to the manufacturer's recommendations. Immobilization resulted in approximately 850, 900 and 1400 resonance units, respectively, for the three molecules. TNF-α samples of different concentrations were injected at a flow rate of 30 µl/min. Five different concentrations (0, 0.25, 0.5, 1 and 2 µM) in HBS-EP (10 mM HEPES, 150 mM NaCl, 3 mM EDTA, 0.005% P-20, pH 7.4) were measured. Injections of TNF-α were made during 5 minutes followed by injection of HBS-EP for 10 minutes. The surfaces were finally regenerated with 2 injections of 10 mM HCl. The response measured in a reference cell was subtracted from the responses measured in the cells containing immobilized ZTNF variants. FIG. 5A-5C shows sensorgrams obtained from the measurements of (Z00734)$_4$ (5A), (Z00752)$_4$ (5B) and (Z00771)$_4$ (5C). The concentrations of TNF-α used in each binding curve of the four sensorgrams are indicated as follows: 0 μM □, 0.25 μM ▶, 0.5 μM Δ, 1 μM ○, 2 μM ◊. Binding values to a blank sensorchip surface have been subtracted. Apparent $K_D$ values were estimated using BIAevaluation 3.2 software (Biacore AB), assuming a 1:1 Langmuir binding model. The approximate $K_D$ for the interaction with TNF-α is 400 nM for all three ZTNF variants.

EXAMPLE 4

De Novo Selection and Flow Cytometry Analysis of TNF-α Binding Polypeptides Using Microbead Display A combinatorial library of Z variants, adopted for microbead display (Nord O et al, J Biotechnol 106:1-13 (2003) and U.S. Pat. No. 6,955,877), was constructed by ligating a library assembly cassette (Nord K et al (1995) Prot Eng 8:601-608) flanked by XhoI and NheI restriction sites into an XhoI and NheI restricted pET-23d-FLAG vector (Nord O et al (2003) supra). Biotinylated PCR fragments encoding the library of Z variants fused to FLAG, prepared for cell-free transcription and translation, was obtained by performing PCR on the ligation mixture with the primers AFFI-808 (SEQ ID NO:91) and AFFI-811 (SEQ ID NO:92).

PCR fragments encoding the library of Z variants were immobilized on 2×10$^8$ streptavidin-coated beads (Bangs Laboratories) at a concentration of approximately 0.60 ng/mg beads, corresponding to approximately 50 PCR fragments per bead, resulting in an Z variant library of 1×10$^{10}$ variants. The beads (50 mg) had previously been incubated with 7.5 μl of a solution containing 1.89 mg/ml of a biotinylated anti-FLAG peptide antibody (BioM5, Sigma, Saint Louis, Mo., USA). The 1×10$^{10}$ library was subjected to 400 μl of a cell-free transcription and translation reaction mix using a PURESYSTEM S-S Standard system (Post Genome Institute Co Ltd, Tokyo, Japan). After incubation for two hours at 30° C. with gentle mixing, the bead library was washed three times with phosphate buffered saline (PBS) with 0.05% Pluronic F108 NF surfactant (BASF Corporation, Mount Olive, N.J., USA). The bead library was subsequently incubated with 100 nM TNF-α (Research Diagnostics Inc, cat no RDI-301-223X, lot no 105HTNFA01X; SEQ ID NO:85) conjugated to Alexa Fluor 488 (Molecular Probes, Eugene, Oreg., USA) to detect those translated and biospecifically bead-immobilized, Z variant molecules fused to FLAG, capable of binding TNF-α-Alexa Fluor 488. After incubation for 30 min in room temperature with gentle mixing, the bead library was washed three times with phosphate buffered saline (PBS; 2.68 mM KCl, 1.47 mM KH$_2$PO$_4$, 137 mM NaCl, 8.1 Na$_2$HPO$_4$, pH 7.4) with 0.05% Pluronic F108 NF surfactant (BASF Corporation, Mount Olive, N.J., USA) and resuspended in PBS for flow cytometric sorting.

Flow cytometric sorting was performed in two steps without any addition of TNF-α-Alexa Fluor 488, using a FACSVantage SE instrument (BD Biosciences, San Jose, Calif., USA). A sorting gate was set to sort out beads with a relative Alexa Fluor 488 fluorescence of ≧20. The first sorting step was performed in enrichment mode (low purity and high yield of the sorted bead fraction) and 21000 beads were collected. During the first sorting step, all sorted beads were collected in the same tube containing PBS. In the second sorting step, stringent purity sorting was performed (high purity and low yield of the sorted bead fraction) and 2600 beads were collected. The PCR fragments on the collected beads from the second sorting step were amplified by PCR with primers AFFI-808 and AFFI-811. The resulting PCR fragments were applied on a 1% agarose gel for gel electrophoresis, and the band corresponding to PCR fragments of correct size was cut out and purified using GenElute Minus EtBr Spin Columns (Sigma, Saint Louis, Mo., USA).

A second selection cycle was performed by immobilizing the purified PCR fragments from the first selection cycle on 2.5×10$^7$ beads at a concentration of 0.012 ng/mg beads, corresponding to approximately one PCR fragment per bead. The beads had previously been incubated with a solution containing a biotinylated anti-FLAG peptide antibody (BioM5) as described above. Subsequently, the beads were subjected to 50 μl of cell-free transcription and translation reaction mix using a PURESYSTEM S-S Standard system, followed by incubation with 100 nM TNF-α conjugated to Alexa Fluor 488 as described above. The beads were washed three times in PBS with 0.05% Pluronic F108 NF surfactant (BASF Corporation, Mount Olive, N.J., USA) and resuspended in PBS for flow cytometric sorting in which a two-step sorting scheme was employed without any addition of TNF-α-Alexa Fluor 488 as described above. From the second sorting step, 1000 beads were collected and a two-step PCR reaction was performed. The first PCR reaction was performed on the collected beads using primers AFFI-808 and AFFI-811. This PCR reaction served as template for a second, nested PCR using the primers AFFI-903 (SEQ ID NO:94) and AFFI-24 (SEQ ID NO:89). The resulting PCR fragments were applied on a 1% agarose gel and purified as described above.

The purified PCR fragments from the second selection cycle were cloned into a pGEM-T vector using the pGEM-T Vector System I (Promega, Madison, Wis., USA) and transformed into *Escherichia coli* strain RRIΔM15 (Ruther U, Nucl Acids Res 10:5765-5772 (1982)). A PCR screen of the resulting colonies after transformation was performed with primers AFFI-21 (SEQ ID NO:86) and AFFI-26 (SEQ ID NO:90) and colonies with PCR fragment-inserts of correct length were amplified and identified by DNA sequencing as described in Example 1 using the primer AFFI-26.

DNA sequencing revealed two clones from the second microbead display selection cycle, denoted Z01446 (SEQ ID NO:76) and Z01447 (SEQ ID NO:77) (FIG. 1). Z01446 and Z01447 were further analyzed by flow cytometric analysis to verify their TNF-α binding activity. PCR was performed on the colonies harboring the clones Z01446 and Z01447 with primers AFFI-902 (SEQ ID NO:93) and AFFI-903, yielding biotinylated PCR fragments enabling cell-free transcription and translation of the two clones. The two PCR fragments were separately immobilized on two set of beads at a concentration of 8 ng/mg beads, corresponding to approximately 500 PCR fragments per bead. The two sets of beads had previously been incubated with a biotinylated anti-FLAG peptide antibody (BioM5) as described above. The two sets of beads with FLAG-Z01446 and FLAG-Z01447 PCR fragments were individually resuspended in 25 μl of cell-free transcription and translation reaction mix, using a PURESYSTEM S-S Standard system followed by incubation with 500 nM TNF-α conjugated to Alexa Fluor 488 as described above. After incubation for 30 min in room temperature with gentle mixing, the two sets of beads were washed as described above and resuspended in PBS for clonal flow cytometric analysis.

Two controls were included in the flow cytometric analysis. The first control comprised streptavidin-coated beads immobilized with biotinylated anti-FLAG peptide antibody (negative control) and the second control comprised streptavidin-coated beads co-immobilized with biotinylated anti-FLAG peptide antibody and biotinylated FLAG-Z00185 PCR fragment (positive control). Z00185 is a TNF-α-binding Z variant identified by phage display as described in Example 1. The FLAG-Z00185 PCR fragment, prepared for cell-free transcription and translation, was generated by performing PCR on a pET-23d-FLAG-Z00185 vector, constructed as described above, using the primers AFFI-808 and AFFI-811.

Figure 6:
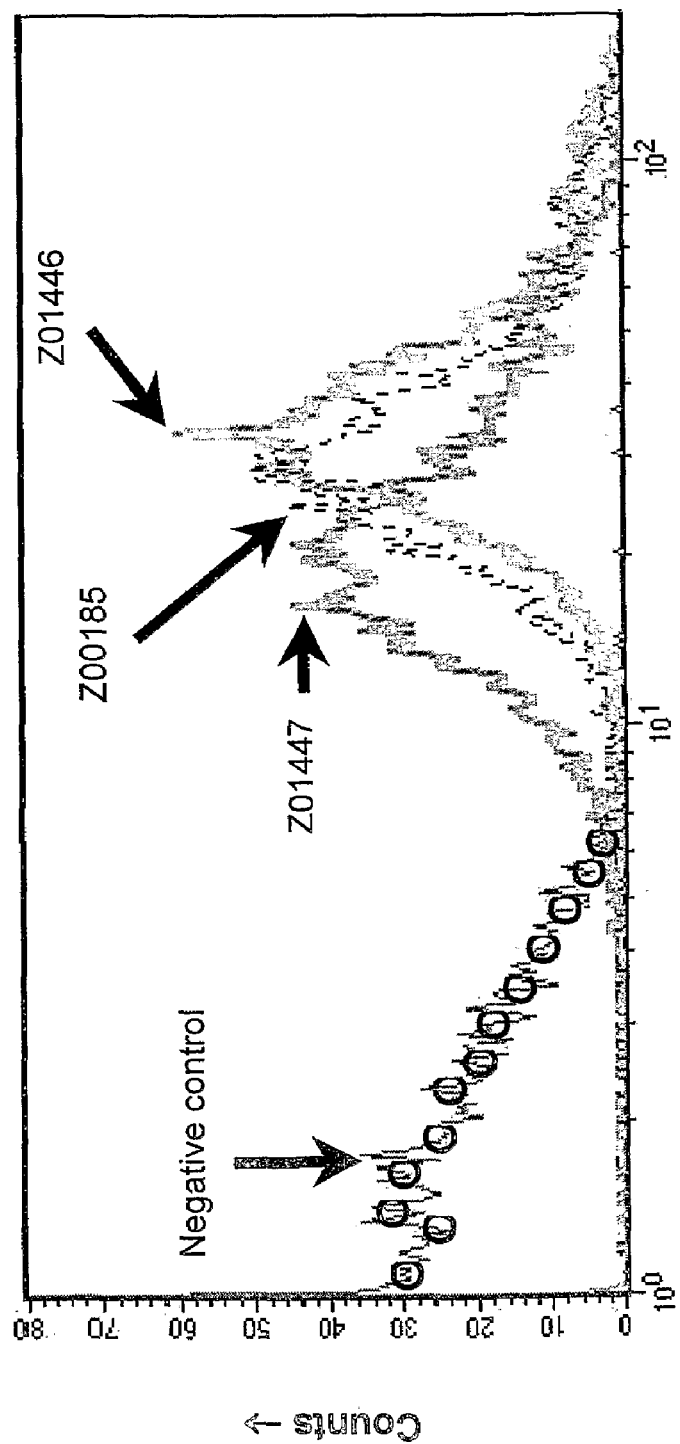
FIG. 6 is a flow cytometric comparative histogram overlay of four sets of beads comprising streptavidin-coated beads with anti-FLAG peptide antibody (BioM5) co-immobilized with biotinylated PCR fragments encoding FLAG-Z01446 fusion protein (solid light grey line), FLAG-Z01447 fusion protein (solid dark grey line), FLAG-Z00185 fusion protein (dashed black line) and negative control beads immobilized with anti-FLAG peptide antibody (BioM5) (grey line with rings), respectively, subjected to cell-free transcription and translation extract followed by incubation with TNF-α-Alexa Fluor 488.

Flow cytometric analysis of Z01446 and Z001447 revealed a significantly higher Alexa Fluor 488 fluorescence compared to the negative control beads (FIG. 6), indicating TNF-α-binding activity of both Z01446 and Z01447. In addition, the fluorescence values for Z01446 and Z01447 were comparable to those for Z00185, which had been previously identified using with phage display and is included for reference in the histogram (FIG. 6).

EXAMPLE 5

De Novo Selection of TNF-α Binding Polypeptides Using Protein Fragment Complementation Assay (PCA)

A combinatorial library of Z variants, adopted for TEM-1 β-lacatamase protein fragment complementation assay (PCA) in *Escherichia coli* (Nord O et al, FEMS Microbiol Lett 242:73-79 (2005)), was constructed by performing PCR on the 129 bp oligonucleotide AFFI-546 (SEQ ID NO:96) encoding helices 1 and 2 of the Z domain. The gene fragment was amplified using the forward primer AFFI-047 (SEQ ID NO:99) and the reverse primer AFFI-050 (SEQ ID NO:100), with 100 fmol template oligonucleotide for each of 95 parallel reactions. The amplifications were performed using AmpliTaq Gold polymerase (Applied Biosystems) for 10 cycles (15 s at 96° C., 15 s at 60° C., 1 min at 72° C.), pooled, purified using the QIAquick PCR purification kit (Qiagen, Hilden, Germany), XhoI/NheI digested and ligated into an XhoI- and NheI-restricted pOmpA-ω198 vector (Nord O et al (2005), supra).

Electrocompetent *E. coli* RRIΔM15 cells (Ruther U (1982), supra) were transformed with 60 aliquots of ligated material using 0.2-cm-gap-size cuvettes in an ECM 630 set (BTX, Genetronics) at 2500 V, 125 W and 50 μF. Cells were grown in SOC medium (Tryptone Soy Broth (TSB)+Yeast Extract (YE) supplemented with 1% glucose, 10 mM $MgCl_2$, 10 mM $MgSO_4$, 10 mM NaCl and 2.5 mM KCl) for 50 min and transferred to 6 E-flasks, each containing 1 l TSB+YE (30 g/l TSB (Merck, Darmstadt, Germany), 5 g/l YE (Merck)) supplemented with 2% glucose and 25 μg/ml carbencillin and grown over night at 37° C. The cells were centrifuged at 2000 g, and then resuspended in PBS/glycerol solution to a final approximate concentration of 20% glycerol, aliquoted and stored at −80° C. This yielded a library of $1.6 \times 10^9$ variants.

A selection against TNF-α was performed by preparing a phage stock (Nord K et al (1995), supra) from the $1.6 \times 10^9$ library. The phage stock was used to infect log-phase ($OD_{600}$=0.5-0.8) *E. coli* RRIΔM15 cells (pre-cultivated in 28 ml TSB with tetracycline (20 μg/ml)) harboring the vector pOmpA-α197-TNF-α (Nord O et al (2005), supra), in which the gene coding for TNF-α (Swiss-Prot accession number P01375) had been inserted between the NotI and AscI restriction sites and the chloramphenicol resistance marker had been replaced with a tetracycline resistance marker. The infection was performed at 37° C. for 2 h without shaking followed by centrifugation. Subsequently, the cell pellet was resuspended in freshly made TSB supplemented with yeast extract, chloramphenicol (20 μg/ml), tetracycline (20 μg/ml) and IPTG (1 mM). After cultivation for 5 h at 37° C., the cells were plated on 20×20 cm agar plates containing different concentrations of carbenecillin (40, 80 and 160 μg/ml), chloramphenicol (20 μg/ml), tetracycline (20 μg/ml), tazobactam (0.4 μg/ml) and IPTG (1 mM). Incubation was performed over night at 37° C., and surviving cells were screened with PCR using primers AFFI-21 (SEQ ID NO:86) and AFFI-617 (SEQ ID NO:98) and DNA sequencing was performed as described in Example 1 using primers AFFI-71 (SEQ ID NO:95) and AFFI-609 (SEQ ID NO:97).

Seven colonies of TNF-α-binding Z variants were identified (SEQ ID NO:78-84; FIG. 1). The seven ZTNF variants were produced as soluble secreted proteins fused to a 5 kDa serum albumin binding protein (ABD), released from the periplasm and purified by affinity chromatography on HSA-sepharose columns (Nygren et al, J Mol Recognit 1:69-74 (1988)).

Figure 7A:
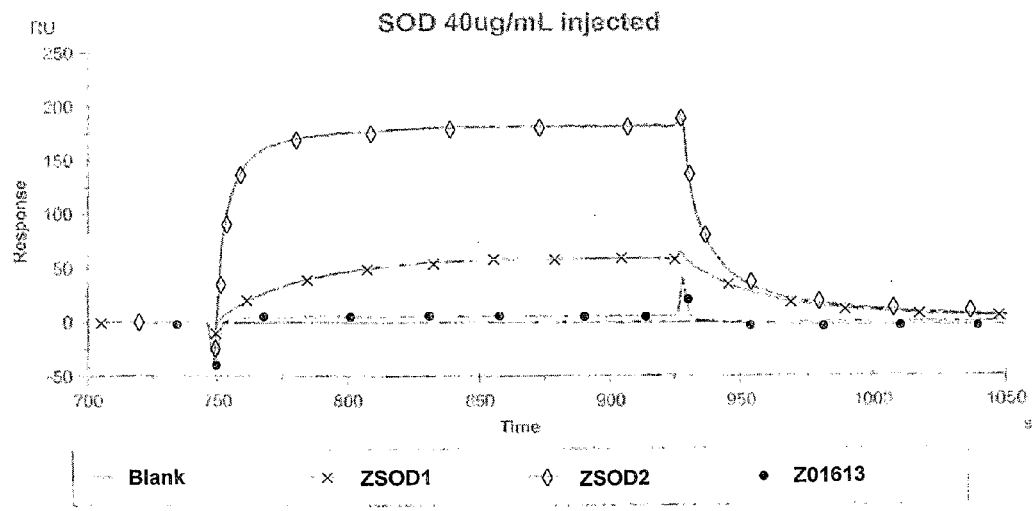
FIGS. 7A-B are comparative sensorgram overlays obtained from biosensor analysis of chip-immobilized Z01613 and two control Z variants denoted ZSOD1 and ZSOD2, including a blank sensor-chip surface. Superoxide dismutase was injected at a concentration of 40 μg/ml (FIG. 7A) and TNF-α at a concentration of 50 μg/ml (FIG. 7B).
Figure 7B:
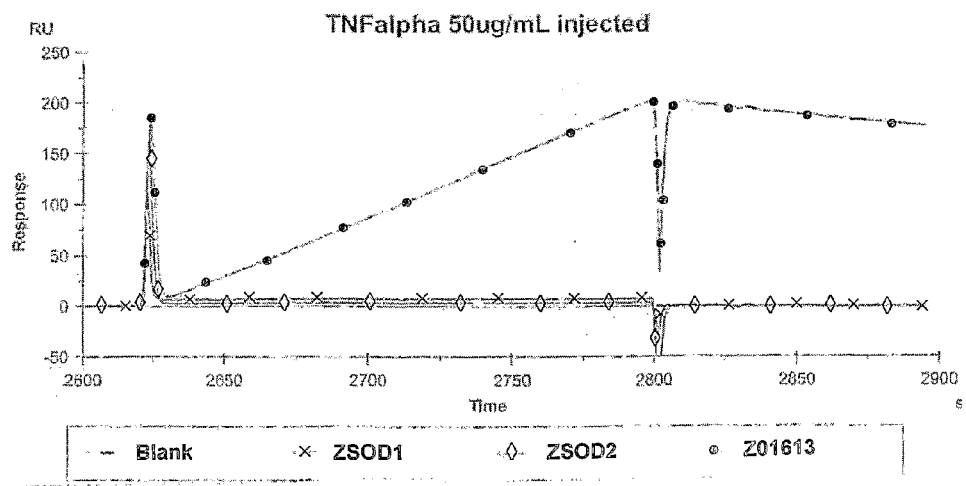
Figure 8A:
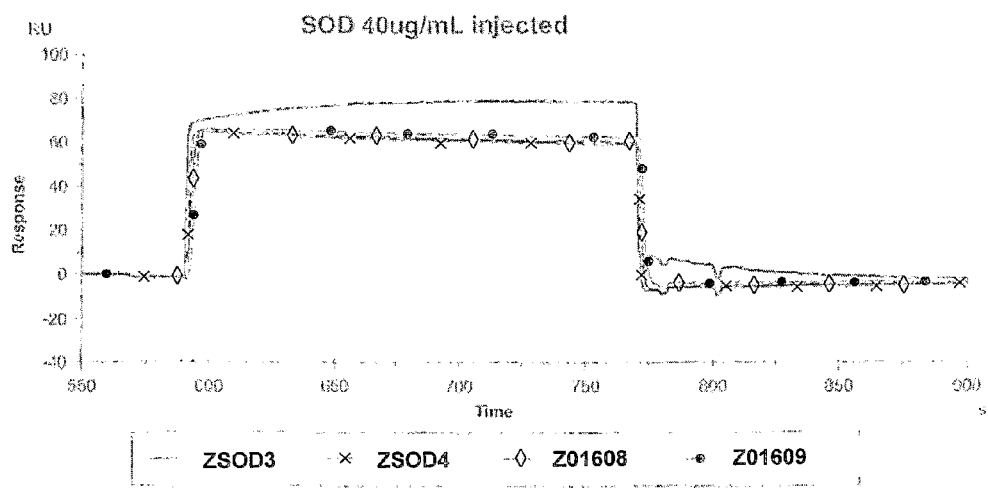
FIGS. 8A-C are comparative sensorgram overlays obtained from biosensor analysis of chip-immobilized Z01608 and Z01609 and two control Z variants denoted ZSOD3 and ZSOD4. Superoxide dismutase was injected at a concentration of 40 μg/ml (FIG. 8A) and 1 mg/ml (FIG. 8B), and TNF-α at a concentration of 50 μg/ml (FIG. 8C).
Figure 8B:
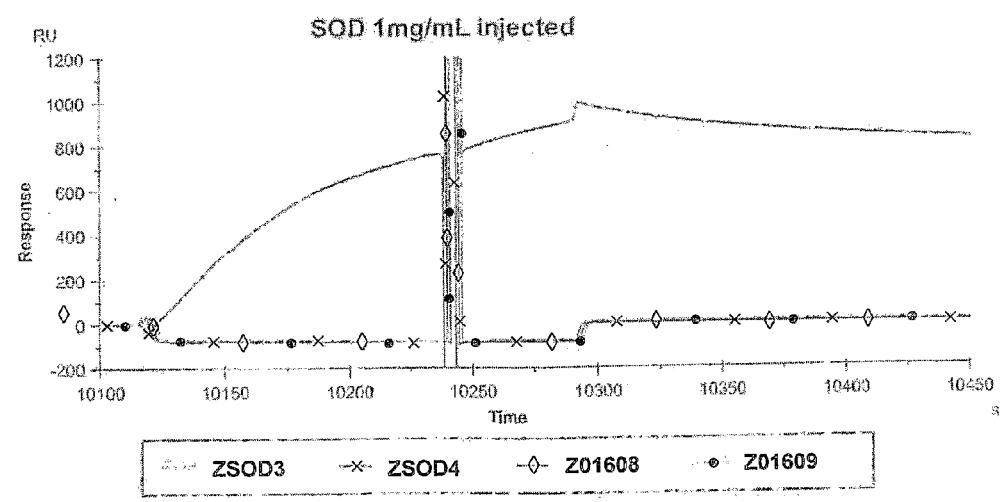
Figure 8C:
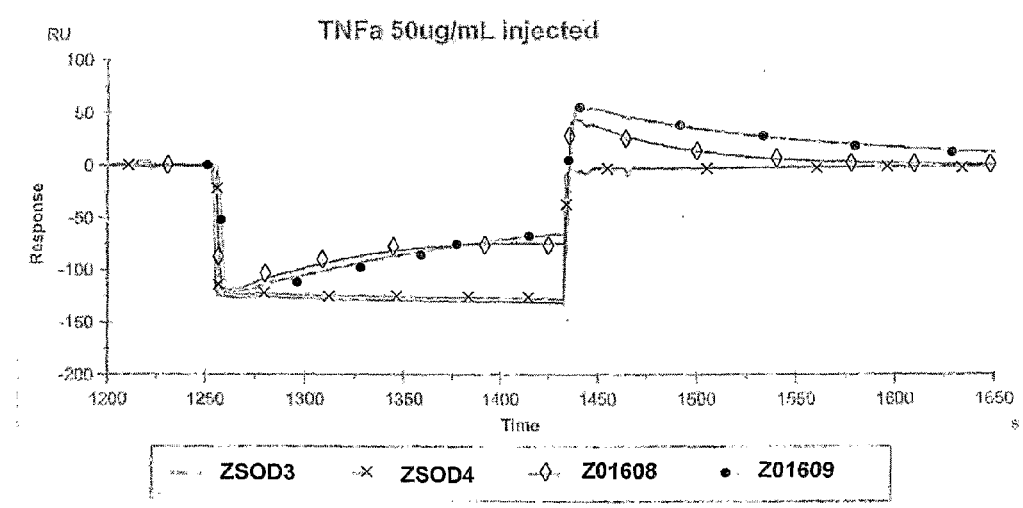
Figure 9A:
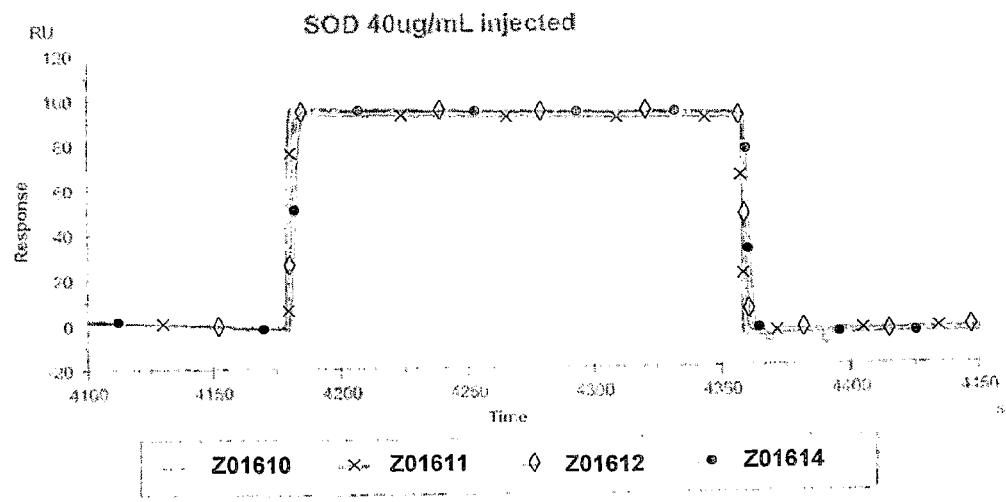
FIGS. 9A-B are comparative sensorgram overlays obtained from biosensor analysis of chip-immobilized Z01610, Z01611, Z01612 and Z01614. Superoxide dismutase was injected at a concentration of 40 μg/ml (FIG. 9A) and TNF-α at a concentration of 50 μg/ml (FIG. 9B).
Figure 9B:
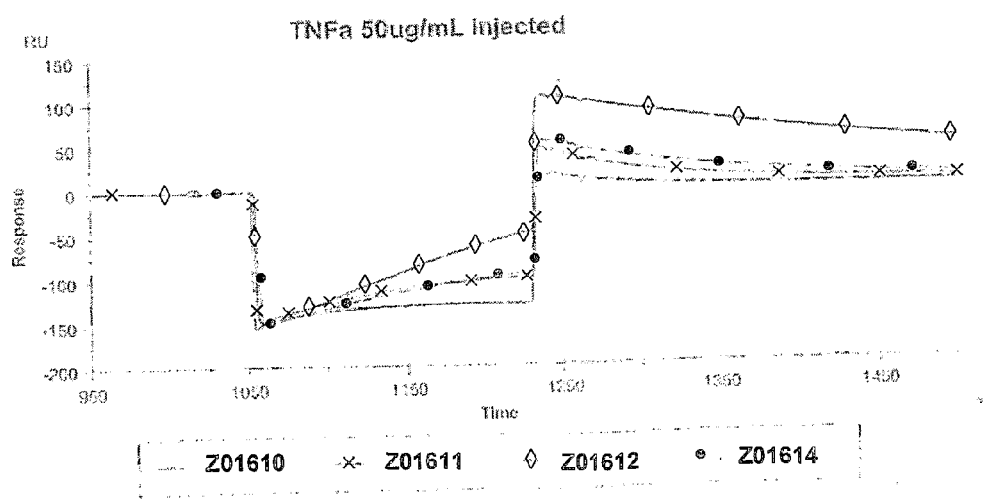

Biosensor analysis of the ZTNF variant fusion proteins Z01608-ABD, Z01609-ABD, Z01610-ABD, Z01611-ABD, Z01612-ABD, Z01613-ABD and Z01614-ABD was performed with a BIAcore™ instrument essentially as described for in Example 3. Briefly, the ZTNF variants were immobilized on a CM-5 chip, including negative control Z variants (Z variants selected for specific binding activity towards superoxide dismutase and denoted ZSOD1, ZSOD2, ZSOD3 and ZSOD4) as indicated in FIGS. 7 and 8. All seven ZTNF molecules, Z01608, Z01609, Z01610, Z01611, Z01612, Z01613 and Z01614, showed TNF-α-binding activity when TNF-α was injected at the indicated concentrations (FIGS. 7B, 8C and 9B).

The invention claimed is:

1. An isolated TNF-α binding polypeptide, which is related to a domain of staphylococcal protein A (SPA), said polypeptide is selected from the group consisting of SEQ ID NO: 2-84.

2. The TNF-α binding polypeptide according to claim 1, which has a binding affinity for TNF-α such that the apparent $K_D$ value of the interaction is at most $1 \times 10^{-7}$ M, as measured by surface plasmon resonance.

3. The TNF-α binding polypeptide according to claim 2, the apparent $K_D$ value of the interaction being at most $5 \times 10^{-8}$ M, as measured by surface plasmon resonance.

4. The TNF-α binding polypeptide according to claim 3, the apparent $K_D$ value of the interaction being at most $1 \times 10^{-8}$ M, as measured by surface plasmon resonance.

5. The TNF-α binding polypeptide according to claim 1, comprising a substitution mutation at a position corresponding to position 32 in SEQ ID NO:1 from glutamine to arginine, and being selected from the group consisting of SEQ ID NO: 4, 8, 10-13, 15, 19, 24, 26-31, 16, 35-40, 42, 46, 48, 50, 53, 56, 61, 64, 66, 67, 70, 73 and 83.

6. The TNF-α binding polypeptide according to claim 1, comprising a substitution mutation at a position corresponding to position 18 in SEQ ID NO:1 from histidine to arginine, and being selected from the group consisting of SEQ ID NO: 4, 6, 13, 30, 32, 34, 36, 38, 45, 47-48, 57-58, 62, 64-65, 67, 75 and 78.

7. The TNF-α binding polypeptide according to claim 1, comprising a substitution mutation at a position corresponding to position 28 in SEQ ID NO:1 from asparagine to an amino acid selected from tyrosine and arginine, and being selected from the group consisting of SEQ ID NO: 3, 5, 16, 20, 25-26, 32-34, 39, 43-45, 49-53, 55-56, 61, 65, 68-69, 71-72, 74, 76 and 81.

8. The TNF-α binding polypeptide according to claim 1, comprising a substitution mutation at a position corresponding to position 27 in SEQ ID NO:1 from arginine to tyrosine, and being selected from the group consisting of SEQ ID NO: 20, 26, 33-34, 39, 44-45, 49-53, 55-56, 61-62, 72, 74 and 81.

9. The TNF-α binding polypeptide according to claim 1, comprising a substitution mutation at a position corresponding to position 25 in SEQ ID NO:1 from glutamic acid to an amino acid residue selected from histidine and glutamine, and being selected from the group consisting of SEQ ID NO: 5, 13-15, 20, 26, 32-34, 38-39, 41, 44-45, 48-56, 61-62, 68, 70, 72 and 76.

10. The TNF-α binding polypeptide according to claim 1, comprising a substitution mutation at a position corresponding to position 17 in SEQ ID NO:1 from leucine to an amino acid residue selected from glycine and alanine, and being selected from the group consisting of SEQ ID NO: 3, 5, 12, 20, 23, 25, 32, 39, 41, 43-47, 52-53, 55-56, 59-61, 68-69, 71-74, 76, 79-81 and 83-84.

11. The TNF-α binding polypeptide according to claim 1, comprising a substitution mutation at a position corresponding to position 13 in SEQ ID NO:1 from phenylalanine to isoleucine, and being selected from the group consisting of SEQ ID NO: 5, 18, 25, 49, 51, 54, 59-61, 69 and 76-77.

12. The TNF-α binding polypeptide according to claim 1, comprising at least one of the following mutations: N3A, N6A, N6D, N11S, N23T, N28A and N43E.

13. The TNF-α binding polypeptide according to claim 1, which comprises additional amino acid residues at either or both termini.

14. The TNF-α binding polypeptide according to claim 13, in which the additional amino acid residues comprise a cysteine residue at the N- or C-terminal of the polypeptide.

15. The TNF-α binding polypeptide according to claim 13, in which the additional amino acid residues comprise a tag, preferably chosen from a hexahistidyl tag, a myc tag and a flag tag.

16. The TNF-α binding polypeptide according to claim 13, in which the additional amino acid residues comprise at least one functional polypeptide domain, so that the polypeptide is a fusion polypeptide between a first moiety, consisting of the polypeptide according to claim 1, and at least one second and optionally further moiety or moieties.

17. The TNF-α binding polypeptide according to claim 16, in which the second moiety consists of one or more polypeptide(s) according to claim 1, making the polypeptide a multimer of TNF-α binding polypeptides.

18. The TNF-α binding polypeptide according to claim 16, in which the second moiety comprises at least one polypeptide domain capable of binding to a target molecule other than TNF-α.

19. The TNF-α binding polypeptide according to claim 18, in which the second moiety comprises at least one polypeptide domain capable of binding to human serum albumin.

20. The TNF-α binding polypeptide according to claim 19, in which the at least one polypeptide domain capable of binding to human serum albumin is an albumin binding domain of streptococcal protein G.

21. The TNF-α binding polypeptide according to claim 16, in which the second moiety is capable of enzymatic action.

22. The TNF-α binding polypeptide according to claim 16, in which the second moiety is capable of fluorescent action.

23. The TNF-α binding polypeptide according to claim 16, in which the second moiety is a phage coat protein or a fragment thereof.

24. The TNF-α binding polypeptide according to claim 1, which comprises a label group.

25. The TNF-α binding polypeptide according to claim 24, in which the label group is chosen from fluorescent labels, biotin and radioactive labels.

26. An isolated nucleic acid molecule comprising a sequence encoding the polypeptide according to claim 1.

27. An expression vector comprising the nucleic acid molecule according to claim 26.

28. A host cell comprising the expression vector according to claim 27.

29. An affinity matrix comprising a polypeptide according to claim 1.

30. A method of separation of TNF-α present in a sample from other constituents in the sample, said method comprising the steps:

a) applying the sample to an affinity matrix comprising a polypeptide according to claim 1 under conditions that are conducive to binding of TNF-α to the affinity matrix;
b) washing the affinity matrix for removal of substances not bound thereto; and
c) eluting the bound TNF-α from the affinity matrix, thus obtaining TNF-α fraction with an enriched TNF-α content; and
d) recovering said TNF-α fraction.

31. A method of separation of TNF-α present in a sample from other constituents in the sample, said method comprising the steps:

a) applying the sample to an affinity matrix comprising a polypeptide according to claim 1 under conditions that are conducive to binding of TNF-α to the affinity matrix;
b) washing the affinity matrix for recovery of substances not bound thereto, thus obtaining a depleted fraction with a substantially reduced TNF-α content; and
c) recovering said depleted fraction.

32. A method of separation of TNF-α present in a sample from other constituents in the sample to yield a depleted fraction, said method comprising the steps:

a) applying the sample to an affinity matrix comprising a polypeptide according to claim 1 under conditions that are conducive to binding of TNF-α to the affinity matrix; and
b) recovering said depleted fraction.

33. A method of separation of TNF-α present in a sample from other constituents in the sample, said method comprising the steps:

a) applying of the sample to an affinity matrix comprising a polypeptide according to claim 1 under conditions that are conducive to binding of TNF-α to the affinity matrix;
b) washing the affinity matrix for recovery of substances not bound thereto, thus obtaining a depleted fraction with a substantially reduced TNF-α content; and
c) eluting the bound TNF-α from the affinity matrix, thus obtaining TNF-α fraction with an enriched TNF-α content; and
d) recovering said TNF-α fraction and said depleted fraction.

34. A method for reducing the content of TNF-α in a portion of a body fluid of a human, comprising:

a) providing a portion of a body fluid from a human;
b) applying the portion of a body fluid to an affinity matrix comprising a polypeptide according to claim 1 under conditions enabling binding of TNF-α to the affinity matrix, thereby causing a reduction of the content of TNF-α in the portion of body fluid.

35. The method according to claim 34, further comprising:

c) returning at least a part of the portion of body fluid to the human.

36. The method according to claim 34, wherein the sample of a body fluid is obtained from a subject afflicted by inflammation.

37. The method according to claim 34, wherein the body fluid is whole blood.

38. The method according to claim 34, wherein the body fluid is plasma.

39. The method according to claim 34, wherein the body fluid is serum.

40. A method for detection of TNF-α in a sample, said method comprising the steps:
   a) providing a sample to be tested,
   b) applying a polypeptide according to claim 1 to the sample under conditions such that binding of the polypeptide to any TNF-α present in the sample is enabled,
   c) removing non-bound polypeptide, and
   d) detecting bound TNF-α.

41. The method according to claim 40, in which the sample is a biological fluid sample, preferably a human blood plasma sample.

42. The method according to claim 40, in which the sample is a tissue sample.

* * * * *

UNITED STATES PATENT AND TRADEMARK OFFICE
CERTIFICATE OF CORRECTION

| | | |
|---|---|---|
| PATENT NO. | : 7,993,848 B2 | Page 1 of 1 |
| APPLICATION NO. | : 11/885373 | |
| DATED | : August 9, 2011 | |
| INVENTOR(S) | : Nina Herne | |

It is certified that error appears in the above-identified patent and that said Letters Patent is hereby corrected as shown below:

Claim 5, Col. 73, line 66: "16" should read --33--.

Signed and Sealed this
Thirteenth Day of December, 2011

David J. Kappos
*Director of the United States Patent and Trademark Office*

SEQUENCE LISTING

```
<160> NUMBER OF SEQ ID NOS: 100

<210> SEQ ID NO 1
<211> LENGTH: 58
<212> TYPE: PRT
<213> ORGANISM: Artificial Sequence
<220> FEATURE:
<223> OTHER INFORMATION: Engineered Sequence

<400> SEQUENCE: 1

Val Asp Asn Lys Phe Asn Lys Glu Gln Gln Asn Ala Phe Tyr Glu Ile
```

```
                1               5                  10                  15
Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 2
<211> LENGTH: 58
<212> TYPE: PRT
<213> ORGANISM: Artificial Sequence
<220> FEATURE:
<223> OTHER INFORMATION: Engineered Sequence

<400> SEQUENCE: 2

```
Val Asp Asn Lys Phe Asn Lys Glu Ala Ala Trp Ala Pro Phe Glu Ile
1               5                   10                  15

Gln His Leu Pro Asn Leu Asn His Pro Gln Asn Asp Ala Phe Ile Asp
                20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 3
<211> LENGTH: 58
<212> TYPE: PRT
<213> ORGANISM: Artificial Sequence
<220> FEATURE:
<223> OTHER INFORMATION: Engineered Sequence

<400> SEQUENCE: 3

```
Val Asp Asn Lys Phe Asn Lys Glu Met Phe Gly Ala Val Gly Glu Ile
1               5                   10                  15

Gly Ala Leu Pro Asn Leu Asn Asp Arg Gln Leu Arg Ala Phe Ile Leu
                20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 4
<211> LENGTH: 58
<212> TYPE: PRT
<213> ORGANISM: Artificial Sequence
<220> FEATURE:
<223> OTHER INFORMATION: Engineered Sequence

<400> SEQUENCE: 4

```
Val Asp Asn Lys Phe Asn Lys Glu Cys Trp Arg Ala Pro Phe Glu Ile
1               5                   10                  15

Tyr Arg Leu Pro Asn Leu Asn Arg Glu Gln Gln Ile Ala Phe Ile Arg
                20                  25                  30

Ser Leu Cys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 5
<211> LENGTH: 58

```
<212> TYPE: PRT
<213> ORGANISM: Artificial Sequence
<220> FEATURE:
<223> OTHER INFORMATION: Engineered Sequence

<400> SEQUENCE: 5

Val Asp Asn Lys Phe Asn Lys Glu Leu Gly Trp Ala Ile Gly Glu Ile
1               5                   10                  15

Gly Thr Leu Pro Asn Leu Asn His Gln Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Engineered Sequence

<400> SEQUENCE: 6

Val Asp Asn Lys Phe Asn Lys Glu Ser Glu Gly Ala Met His Glu Ile
1               5                   10                  15

Val Arg Leu Pro Asn Leu Asn Ala Trp Gln Arg Gln Ala Phe Ile Val
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Engineered Sequence

<400> SEQUENCE: 7

Val Asp Asn Lys Phe Asn Lys Glu Lys Lys Met Ala Ala Cys Glu Ile
1               5                   10                  15

Gln Gly Leu Pro Asn Leu Asn Ile Asp Gln Cys Trp Ala Phe Ile Thr
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Engineered Sequence

<400> SEQUENCE: 8

Val Asp Asn Lys Phe Asn Lys Glu Met Gln Cys Ala Gly Cys Glu Ile
1               5                   10                  15

Gln Asp Leu Pro Asn Leu Asn Ile Glu Gln Cys Cys Ala Phe Ile Arg
            20                  25                  30

Ser Leu Arg Asp Asp Pro Ser Gln Ser Ala Asn Leu Leu Ala Glu Ala
```

```
                        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Engineered Sequence

<400> SEQUENCE: 9

Val Asp Asn Lys Phe Asn Lys Glu Gly Arg Thr Ala Ala Cys Glu Ile
1               5                   10                  15

Gln Asp Leu Pro Asn Leu Asn Leu Asp Gln Cys Trp Ala Phe Ile Lys
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Artificial Sequence
<220> FEATURE:
<223> OTHER INFORMATION: Engineered Sequence

<400> SEQUENCE: 10

Val Asp Asn Lys Phe Asn Lys Glu Cys Ser Met Ala Pro Arg Glu Ile
1               5                   10                  15

Trp Ala Leu Pro Asn Leu Asn Arg Glu Gln Ala Val Ala Phe Ile Arg
            20                  25                  30

Ser Leu Cys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Engineered Sequence

<400> SEQUENCE: 11

Val Asp Asn Lys Phe Asn Lys Glu Cys Arg Thr Ala Pro Arg Glu Ile
1               5                   10                  15

Phe Ser Leu Pro Asn Leu Asn Ile Gly Gln Gln Trp Ala Phe Ile Arg
            20                  25                  30

Ser Leu Cys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: Engineered Sequence

<400> SEQUENCE: 12
```

Val Asp Asn Lys Phe Asn Lys Glu Thr Val Pro Ala Met Arg Glu Ile
1               5                   10                  15

Ala Ser Leu Pro Asn Leu Asn Thr Thr Gln Lys Val Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Engineered Sequence

<400> SEQUENCE: 13

Val Asp Asn Lys Phe Asn Lys Glu Cys Ala Tyr Ala Pro Arg Glu Ile
1               5                   10                  15

Trp Arg Leu Pro Asn Leu Asn His Gln Gln Gly Val Ala Phe Ile Arg
            20                  25                  30

Ser Leu Cys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Engineered Sequence

<400> SEQUENCE: 14

Val Asp Asn Lys Phe Asn Lys Glu Pro Asn Val Ala Ser Met Glu Ile
1               5                   10                  15

Leu Pro Leu Pro Asn Leu Asn Asn Gln Gln Met Thr Ala Phe Ile Gln
            20                  25                  30

Ser Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Artificial Sequence
<220> FEATURE:
<223> OTHER INFORMATION: Engineered Sequence

<400> SEQUENCE: 15

Val Asp Asn Lys Phe Asn Lys Glu Arg Val Ala Ala Ala Cys Glu Ile
1               5                   10                  15

Glu Ser Leu Pro Asn Leu Asn Leu Gln Gln Cys Trp Ala Phe Ile Arg
            20                  25                  30

Ser Leu Met Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 16
<211> LENGTH: 58
<212> TYPE: PRT
<213> ORGANISM: Artificial Sequence
<220> FEATURE:
<223> OTHER INFORMATION: Engineered Sequence

<400> SEQUENCE: 16

Val Asp Asn Lys Phe Asn Lys Glu Cys Phe Met Ala Pro Gln Glu Ile
 1               5                  10                  15

Asn Lys Leu Pro Asn Leu Asn Ala Trp Gln Lys Tyr Ala Phe Ile Trp
             20                  25                  30

Ser Leu Cys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 17
<211> LENGTH: 58
<212> TYPE: PRT
<213> ORGANISM: Artificial Sequence
<220> FEATURE:
<223> OTHER INFORMATION: Engineered Sequence

<400> SEQUENCE: 17

Val Asp Asn Lys Phe Asn Lys Glu Gln Ser Ser Ala Met His Glu Ile
 1               5                  10                  15

Val Gln Leu Pro Asn Leu Asn Pro Leu Gln Arg Ala Ala Phe Ile His
             20                  25                  30

Ser Leu Trp Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 18
<211> LENGTH: 58
<212> TYPE: PRT
<213> ORGANISM: Artificial Sequence
<220> FEATURE:
<223> OTHER INFORMATION: Engineered Sequence

<400> SEQUENCE: 18

Val Asp Asn Lys Phe Asn Lys Glu Phe Val Tyr Ala Ile Ala Glu Ile
 1               5                  10                  15

Met Asn Leu Pro Asn Leu Asn Gln Ser Gln Gln Leu Ala Phe Ile Tyr
             20                  25                  30

Ser Leu Arg Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 19
<211> LENGTH: 58
<212> TYPE: PRT
<213> ORGANISM: Artificial Sequence
<220> FEATURE:
<223> OTHER INFORMATION: Engineered Sequence

<400> SEQUENCE: 19

Val Asp Asn Lys Phe Asn Lys Glu Lys Gln Ile Ala Ala Cys Glu Ile
 1               5                  10                  15

Met Asp Leu Pro Asn Leu Asn Gln Asp Gln Cys Phe Ala Phe Ile Arg
             20                  25                  30
```

-continued

Ser Leu Arg Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 20
<211> LENGTH: 58
<212> TYPE: PRT
<213> ORGANISM: Artificial Sequence
<220> FEATURE:
<223> OTHER INFORMATION: Engineered Sequence

<400> SEQUENCE: 20

Val Asp Asn Lys Phe Asn Lys Glu Lys Gly Arg Ala Thr Gly Glu Ile
 1               5                  10                  15

Gly Ala Leu Pro Asn Leu Asn Pro Gln Gln Tyr Arg Ala Phe Ile Leu
             20                  25                  30

Ser Leu His Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 21
<211> LENGTH: 58
<212> TYPE: PRT
<213> ORGANISM: Artificial Sequence
<220> FEATURE:
<223> OTHER INFORMATION: Engineered Sequence

<400> SEQUENCE: 21

Val Asp Asn Lys Phe Asn Lys Glu His Met Glu Ala Asp Cys Glu Ile
 1               5                  10                  15

Glu His Leu Pro Asn Leu Asn Arg Lys Gln Cys Trp Ala Phe Ile Lys
             20                  25                  30

Ser Leu Arg Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 22
<211> LENGTH: 58
<212> TYPE: PRT
<213> ORGANISM: Artificial Sequence
<220> FEATURE:
<223> OTHER INFORMATION: Engineered Sequence

<400> SEQUENCE: 22

Val Asp Asn Lys Phe Asn Lys Glu Arg Thr Val Ala Ser Cys Glu Ile
 1               5                  10                  15

Glu His Leu Pro Asn Leu Asn Leu Asp Gln Cys Trp Ala Phe Ile Asp
             20                  25                  30

Ser Leu Arg Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 23
<211> LENGTH: 58
<212> TYPE: PRT
<213> ORGANISM: Artificial Sequence
<220> FEATURE:
<223> OTHER INFORMATION: Engineered Sequence

<400> SEQUENCE: 23

Val Asp Asn Lys Phe Asn Lys Glu Ser Ala His Ala Val Gly Glu Ile
1               5                   10                  15

Gly Ser Leu Pro Asn Leu Asn Leu Val Gln Ile Gly Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Engineered Sequence

<400> SEQUENCE: 24

Val Asp Asn Lys Phe Asn Lys Glu Gly Arg Pro Ala Gly Leu Glu Ile
1               5                   10                  15

Met Cys Leu Pro Asn Leu Asn Thr Ala Gln Met Val Ala Phe Ile Arg
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Engineered Sequence

<400> SEQUENCE: 25

Val Asp Asn Lys Phe Asn Lys Glu Ser Ala His Ala Ile Gly Glu Ile
1               5                   10                  15

Ala Asn Leu Pro Asn Leu Asn Gly Gly Gln Leu Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Engineered Sequence

<400> SEQUENCE: 26

Val Asp Asn Lys Phe Asn Lys Glu Arg Gln Gln Ala Leu Gly Glu Ile
1               5                   10                  15

Ser Ala Leu Pro Asn Leu Asn Leu His Gln Tyr Tyr Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 27
<211> LENGTH: 58
<212> TYPE: PRT
<213> ORGANISM: Artificial Sequence
<220> FEATURE:
<223> OTHER INFORMATION: Engineered Sequence

<400> SEQUENCE: 27

Val Asp Asn Lys Phe Asn Lys Glu Ile Val Tyr Ala Pro Arg Glu Ile
1               5                   10                  15

Phe His Leu Pro Asn Leu Asn Ile Leu Gln Gln Ile Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: Engineered Sequence

<400> SEQUENCE: 28

Val Asp Asn Lys Phe Asn Lys Glu Ser Asn Lys Ala Pro Cys Glu Ile
1               5                   10                  15

Gln Asp Leu Pro Asn Leu Asn Ile Asp Gln Cys Ile Ala Phe Ile Arg
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Engineered Sequence

<400> SEQUENCE: 29

Val Asp Asn Lys Phe Asn Lys Glu Phe His Gly Ala Leu Arg Glu Ile
1               5                   10                  15

Trp Lys Leu Pro Asn Leu Asn Val Arg Gln Ala Met Ala Phe Ile Arg
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: Engineered Sequence

<400> SEQUENCE: 30

Val Asp Asn Lys Phe Asn Lys Glu Val Leu Gln Ala Pro Gln Glu Ile
1               5                   10                  15

His Arg Leu Pro Asn Leu Asn Leu Ile Gln Lys Met Ala Phe Ile Arg
            20                  25                  30

Ser Leu Met Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 31
<211> LENGTH: 58
<212> TYPE: PRT
<213> ORGANISM: Artificial Sequence
<220> FEATURE:
<223> OTHER INFORMATION: Engineered Sequence

<400> SEQUENCE: 31

Val Asp Asn Lys Phe Asn Lys Glu Met His Ile Ala Leu Gln Glu Ile
1               5                   10                  15

Tyr Ala Leu Pro Asn Leu Asn Ile Ala Gln Ser Val Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: Engineered Sequence

<400> SEQUENCE: 32

Val Asp Asn Lys Phe Asn Lys Glu Gly Tyr Lys Ala Leu Gly Glu Ile
1               5                   10                  15

Gly Arg Leu Pro Asn Leu Asn Ala Gln Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Engineered Sequence

<400> SEQUENCE: 33

Val Asp Asn Lys Phe Asn Lys Glu Ser Pro Gly Ala Leu Ser Glu Ile
1               5                   10                  15

Met Ala Leu Pro Asn Leu Asn Val His Gln Tyr Tyr Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 34
<211> LENGTH: 58
<212> TYPE: PRT
<213> ORGANISM: Artificial Sequence

```
<220> FEATURE:
<223> OTHER INFORMATION: Engineered Sequence

<400> SEQUENCE: 34

Val Asp Asn Lys Phe Asn Lys Glu Ser Met Ser Ala Ala Leu Glu Ile
1               5                   10                  15

Thr Arg Leu Pro Asn Leu Asn Val His Gln Tyr Tyr Ala Phe Ile Thr
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 35
<211> LENGTH: 58
<212> TYPE: PRT
<213> ORGANISM: Artificial Sequence
<220> FEATURE:
<223> OTHER INFORMATION: Engineered Sequence

<400> SEQUENCE: 35

Val Asp Asn Lys Phe Asn Lys Glu Phe Val Ser Ala Pro Arg Glu Ile
1               5                   10                  15

His Gly Leu Pro Asn Leu Asn Val Thr Gln Arg Met Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 36
<211> LENGTH: 58
<212> TYPE: PRT
<213> ORGANISM: Artificial Sequence
<220> FEATURE:
<223> OTHER INFORMATION: Engineered Sequence

<400> SEQUENCE: 36

Val Asp Asn Lys Phe Asn Lys Glu Cys Trp Met Ala Pro Lys Glu Ile
1               5                   10                  15

Tyr Arg Leu Pro Asn Leu Asn Asp Trp Gln Arg Ser Ala Phe Ile Arg
            20                  25                  30

Ser Leu Cys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Engineered Sequence

<400> SEQUENCE: 37

Val Asp Asn Lys Phe Asn Lys Glu Gly Arg Gly Ala Arg Met Glu Ile
1               5                   10                  15

Val Cys Leu Pro Asn Leu Asn Trp Arg Gln Thr Val Ala Phe Ile Arg
            20                  25                  30

Ser Leu Gln Asp Asp Pro Ser Gln Ser Ala Asn Leu Leu Ala Glu Ala
        35                  40                  45
```

```
Lys Lys Leu Asn Asp Ala Gln Ala Pro Lys
    50                  55

<210> SEQ ID NO 38
<211> LENGTH: 58
<212> TYPE: PRT
<213> ORGANISM: Artificial Sequence
<220> FEATURE:
<223> OTHER INFORMATION: Engineered Sequence

<400> SEQUENCE: 38

Val Asp Asn Lys Phe Asn Lys Glu Gly His Gln Ala Leu Val Glu Ile
1               5                   10                  15

Phe Arg Leu Pro Asn Leu Asn Val Gln Gln Ala Thr Ala Phe Ile Arg
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 39
<211> LENGTH: 58
<212> TYPE: PRT
<213> ORGANISM: Artificial Sequence
<220> FEATURE:
<223> OTHER INFORMATION: Engineered Sequence

<400> SEQUENCE: 39

Val Asp Asn Lys Phe Asn Lys Glu Val Thr Val Ala Gly Val Glu Ile
1               5                   10                  15

Gly Gln Leu Pro Asn Leu Asn Leu His Gln Tyr Tyr Ala Phe Ile Arg
                20                  25                  30

Ser Leu Leu Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 40
<211> LENGTH: 58
<212> TYPE: PRT
<213> ORGANISM: Artificial Sequence
<220> FEATURE:
<223> OTHER INFORMATION: Engineered Sequence

<400> SEQUENCE: 40

Val Asp Asn Lys Phe Asn Lys Glu Val His Gln Ala Leu Arg Glu Ile
1               5                   10                  15

Phe Gln Leu Pro Asn Leu Asn Leu Asp Gln Ser Ile Ala Phe Ile Arg
                20                  25                  30

Ser Leu Ala Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 41
<211> LENGTH: 58
<212> TYPE: PRT
<213> ORGANISM: Artificial Sequence
<220> FEATURE:
<223> OTHER INFORMATION: Engineered Sequence

<400> SEQUENCE: 41

Val Asp Asn Lys Phe Asn Lys Glu Thr Ala Gln Ala Leu Gly Glu Ile
1               5                   10                  15
```

```
                1               5                   10                  15
        Gly Val Leu Pro Asn Leu Asn Ala Gln Gln Ala Ala Phe Ile Leu
                        20                  25                  30

Ser Leu Trp Asp Asp Pro Ser Gln Ser Ala Asn Leu Leu Ala Glu Ala
                        35                  40                  45

Lys Lys Leu Asn Asp Ala Gln Ala Pro Lys
                        50                  55
```

<210> SEQ ID NO 42
<211> LENGTH: 58
<212> TYPE: PRT
<213> ORGANISM: Artificial Sequence
<220> FEATURE:
<223> OTHER INFORMATION: Engineered Sequence

<400> SEQUENCE: 42

```
        Val Asp Asn Lys Phe Asn Lys Glu Gly His Met Ala Val Arg Glu Ile
        1               5                   10                  15

His Gly Leu Pro Asn Leu Asn Val Ala Gln Arg Met Ala Phe Ile Arg
                        20                  25                  30

Ser Leu Val Asp Asp Pro Ser Gln Ser Ala Asn Leu Leu Ala Glu Ala
                        35                  40                  45

Lys Lys Leu Asn Asp Ala Gln Ala Pro Lys
                        50                  55
```

<210> SEQ ID NO 43
<211> LENGTH: 58
<212> TYPE: PRT
<213> ORGANISM: Artificial Sequence
<220> FEATURE:
<223> OTHER INFORMATION: Engineered Sequence

<400> SEQUENCE: 43

```
        Val Asp Asn Lys Phe Asn Lys Glu Val Ala Gln Ala Val Gly Glu Ile
        1               5                   10                  15

Gly Leu Leu Pro Asn Leu Asn Ala Leu Gln Phe Arg Ala Phe Ile Leu
                        20                  25                  30

Ser Leu Leu Asp Asp Pro Ser Gln Ser Ala Asn Leu Leu Ala Glu Ala
                        35                  40                  45

Lys Lys Leu Asn Asp Ala Gln Ala Pro Lys
                        50                  55
```

<210> SEQ ID NO 44
<211> LENGTH: 58
<212> TYPE: PRT
<213> ORGANISM: Artificial Sequence
<220> FEATURE:
<223> OTHER INFORMATION: Engineered Sequence

<400> SEQUENCE: 44

```
        Val Asp Asn Lys Phe Asn Lys Glu Thr Gln Gln Ala Val Leu Glu Ile
        1               5                   10                  15

Gly Thr Leu Pro Asn Leu Asn Ile His Gln Tyr Tyr Ala Phe Ile Lys
                        20                  25                  30

Ser Leu Leu Asp Asp Pro Ser Gln Ser Ala Asn Leu Leu Ala Glu Ala
                        35                  40                  45

Lys Lys Leu Asn Asp Ala Gln Ala Pro Lys
                        50                  55
```

<210> SEQ ID NO 45
<211> LENGTH: 58

```
<212> TYPE: PRT
<213> ORGANISM: Artificial Sequence
<220> FEATURE:
<223> OTHER INFORMATION: Engineered Sequence

<400> SEQUENCE: 45

Val Asp Asn Lys Phe Asn Lys Glu Lys Leu His Ala Ala Gln Glu Ile
 1               5                  10                  15

Gly Arg Leu Pro Asn Leu Asn Val His Gln Tyr Tyr Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: Engineered Sequence

<400> SEQUENCE: 46

Val Asp Asn Lys Phe Asn Lys Glu Val Ala Ala Ala Val Gly Glu Ile
 1               5                  10                  15

Gly Ser Leu Pro Asn Leu Asn Val Gly Gln Phe Ala Ala Phe Ile Arg
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 47
<211> LENGTH: 58
<212> TYPE: PRT
<213> ORGANISM: Artificial Sequence
<220> FEATURE:
<223> OTHER INFORMATION: Engineered Sequence

<400> SEQUENCE: 47

Val Asp Asn Lys Phe Asn Lys Glu Val Val Gly Ala Met Leu Glu Ile
 1               5                  10                  15

Ala Arg Leu Pro Asn Leu Asn Arg Gly Gln Val Asn Ala Phe Ile Trp
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 48
<211> LENGTH: 58
<212> TYPE: PRT
<213> ORGANISM: Artificial Sequence
<220> FEATURE:
<223> OTHER INFORMATION: Engineered Sequence

<400> SEQUENCE: 48

Val Asp Asn Lys Phe Asn Lys Glu Ser Trp Gln Ala Val Pro Glu Ile
 1               5                  10                  15

Phe Arg Leu Pro Asn Leu Asn Val Gln Gln Ser Ile Ala Phe Ile Arg
            20                  25                  30

Ser Leu Val Asp Asp Pro Ser Gln Ser Ala Asn Leu Leu Ala Glu Ala
```

```
                35                  40                  45

Lys Lys Leu Asn Asp Ala Gln Ala Pro Lys
    50                  55

<210> SEQ ID NO 49
<211> LENGTH: 58
<212> TYPE: PRT
<213> ORGANISM: Artificial Sequence
<220> FEATURE:
<223> OTHER INFORMATION: Engineered Sequence

<400> SEQUENCE: 49

Val Asp Asn Lys Phe Asn Lys Glu Leu Glu Arg Ala Ile Phe Glu Ile
  1               5                  10                  15

Ser Asn Leu Pro Asn Leu Asn Leu His Gln Tyr Tyr Ala Phe Ile Thr
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 50
<211> LENGTH: 58
<212> TYPE: PRT
<213> ORGANISM: Artificial Sequence
<220> FEATURE:
<223> OTHER INFORMATION: Engineered Sequence

<400> SEQUENCE: 50

Val Asp Asn Lys Phe Asn Lys Glu Pro Leu Ala Ala Val Met Glu Ile
  1               5                  10                  15

Val Gln Leu Pro Asn Leu Asn Met His Gln Tyr Tyr Ala Phe Ile Arg
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 51
<211> LENGTH: 58
<212> TYPE: PRT
<213> ORGANISM: Artificial Sequence
<220> FEATURE:
<223> OTHER INFORMATION: Engineered Sequence

<400> SEQUENCE: 51

Val Asp Asn Lys Phe Asn Lys Glu Thr Glu Trp Ala Ile Ala Glu Ile
  1               5                  10                  15

Ile Gly Leu Pro Asn Leu Asn Leu His Gln Tyr Tyr Ala Phe Ile Met
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 52
<211> LENGTH: 58
<212> TYPE: PRT
<213> ORGANISM: Artificial Sequence
<220> FEATURE:
<223> OTHER INFORMATION: Engineered Sequence

<400> SEQUENCE: 52
```

```
Val Asp Asn Lys Phe Asn Lys Glu Ala Tyr Thr Ala Ser Leu Glu Ile
 1               5                  10                  15

Ala Asn Leu Pro Asn Leu Asn Met His Gln Tyr Tyr Ala Phe Ile His
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 53
<211> LENGTH: 58
<212> TYPE: PRT
<213> ORGANISM: Artificial Sequence
<220> FEATURE:
<223> OTHER INFORMATION: Engineered Sequence

<400> SEQUENCE: 53

```
Val Asp Asn Lys Phe Asn Lys Glu Met Arg Trp Ala Ala Leu Glu Ile
 1               5                  10                  15

Ala Ala Leu Pro Asn Leu Asn Val His Gln Tyr Tyr Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 54
<211> LENGTH: 58
<212> TYPE: PRT
<213> ORGANISM: Artificial Sequence
<220> FEATURE:
<223> OTHER INFORMATION: Engineered Sequence

<400> SEQUENCE: 54

```
Val Asp Asn Lys Phe Asn Lys Glu Phe His Gly Ala Ile Arg Glu Ile
 1               5                  10                  15

His Leu Leu Pro Asn Leu Asn Leu Gln Gln Arg Met Ala Phe Ile Ile
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 55
<211> LENGTH: 58
<212> TYPE: PRT
<213> ORGANISM: Artificial Sequence
<220> FEATURE:
<223> OTHER INFORMATION: Engineered Sequence

<400> SEQUENCE: 55

```
Val Asp Asn Lys Phe Asn Lys Glu Trp Lys Ala Ala Ala Arg Glu Ile
 1               5                  10                  15

Gly Ser Leu Pro Asn Leu Asn Leu His Gln Tyr Tyr Ala Phe Ile Val
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 56
<211> LENGTH: 58
<212> TYPE: PRT
<213> ORGANISM: Artificial Sequence
<220> FEATURE:
<223> OTHER INFORMATION: Engineered Sequence

<400> SEQUENCE: 56

Val Asp Asn Lys Phe Asn Lys Glu Thr Glu Gln Ala Ala Trp Glu Ile
1               5                   10                  15

Ala Ile Leu Pro Asn Leu Asn Met His Gln Tyr Tyr Ala Phe Ile Arg
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 57
<211> LENGTH: 58
<212> TYPE: PRT
<213> ORGANISM: Artificial Sequence
<220> FEATURE:
<223> OTHER INFORMATION: Engineered Sequence

<400> SEQUENCE: 57

Val Asp Asn Lys Phe Asn Lys Glu Asp Arg Arg Ala Pro Gly Glu Ile
1               5                   10                  15

Val Arg Leu Pro Asn Leu Asn Trp Asp Gln Met Ala Ala Phe Ile Val
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 58
<211> LENGTH: 58
<212> TYPE: PRT
<213> ORGANISM: Artificial Sequence
<220> FEATURE:
<223> OTHER INFORMATION: Engineered Sequence

<400> SEQUENCE: 58

Val Asp Asn Lys Phe Asn Lys Glu Thr Ala Arg Ala Ala His Glu Ile
1               5                   10                  15

Val Arg Leu Pro Asn Leu Asn Pro Arg Gln Arg Ala Ala Phe Ile Thr
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 59
<211> LENGTH: 58
<212> TYPE: PRT
<213> ORGANISM: Artificial Sequence
<220> FEATURE:
<223> OTHER INFORMATION: Engineered Sequence

<400> SEQUENCE: 59

Val Asp Asn Lys Phe Asn Lys Glu Met Phe Ser Ala Ile Gly Glu Ile
1               5                   10                  15

Gly Asn Leu Pro Asn Leu Asn Asp Arg Gln Leu Ala Ala Phe Ile Leu
            20                  25                  30
```

```
Ser Leu Phe Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 60
<211> LENGTH: 58
<212> TYPE: PRT
<213> ORGANISM: Artificial Sequence
<220> FEATURE:
<223> OTHER INFORMATION: Engineered Sequence

<400> SEQUENCE: 60

Val Asp Asn Lys Phe Asn Lys Glu Thr Phe His Ala Ile Gly Glu Ile
 1               5                  10                  15

Gly Ser Leu Pro Asn Leu Asn Asp Met Gln Phe Ser Ala Phe Ile Ile
                20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 61
<211> LENGTH: 58
<212> TYPE: PRT
<213> ORGANISM: Artificial Sequence
<220> FEATURE:
<223> OTHER INFORMATION: Engineered Sequence

<400> SEQUENCE: 61

Val Asp Asn Lys Phe Asn Lys Glu Asn Arg Glu Ala Ile Val Glu Ile
 1               5                  10                  15

Ala Glu Leu Pro Asn Leu Asn Met His Gln Tyr Tyr Ala Phe Ile Arg
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 62
<211> LENGTH: 58
<212> TYPE: PRT
<213> ORGANISM: Artificial Sequence
<220> FEATURE:
<223> OTHER INFORMATION: Engineered Sequence

<400> SEQUENCE: 62

Val Asp Asn Lys Phe Asn Lys Glu Gly Ser Lys Ala Leu Met Glu Ile
 1               5                  10                  15

Ile Arg Leu Pro Asn Leu Asn Val His Gln Tyr Val Ala Phe Ile Met
                20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 63
<211> LENGTH: 58
<212> TYPE: PRT
<213> ORGANISM: Artificial Sequence
<220> FEATURE:
<223> OTHER INFORMATION: Engineered Sequence
```

<400> SEQUENCE: 63

Val Asp Asn Lys Phe Asn Lys Glu Ala Pro Gly Ala Thr Ser Glu Ile
1               5                   10                  15

Asn Ile Leu Pro Asn Leu Asn Trp Arg Gln Ile Met Ala Phe Ile Val
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 64
<211> LENGTH: 58
<212> TYPE: PRT
<213> ORGANISM: Artificial Sequence
<220> FEATURE:
<223> OTHER INFORMATION: Engineered Sequence

<400> SEQUENCE: 64

Val Asp Asn Lys Phe Asn Lys Glu Phe Ile Asp Ala Pro Arg Glu Ile
1               5                   10                  15

Leu Arg Leu Pro Asn Leu Asn Met Thr Gln Gln Met Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 65
<211> LENGTH: 58
<212> TYPE: PRT
<213> ORGANISM: Artificial Sequence
<220> FEATURE:
<223> OTHER INFORMATION: Engineered Sequence

<400> SEQUENCE: 65

Val Asp Asn Lys Phe Asn Lys Glu Thr Met Ala Ala Met Asn Glu Ile
1               5                   10                  15

Val Arg Leu Pro Asn Leu Asn Gly Trp Gln Arg Tyr Ala Phe Ile Gln
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 66
<211> LENGTH: 58
<212> TYPE: PRT
<213> ORGANISM: Artificial Sequence
<220> FEATURE:
<223> OTHER INFORMATION: Engineered Sequence

<400> SEQUENCE: 66

Val Asp Asn Lys Phe Asn Lys Glu Ala His Ser Ala Leu Arg Glu Ile
1               5                   10                  15

Leu Lys Leu Pro Asn Leu Asn Ile Glu Gln Trp Gln Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 67
<211> LENGTH: 58
<212> TYPE: PRT
<213> ORGANISM: Artificial Sequence
<220> FEATURE:
<223> OTHER INFORMATION: Engineered Sequence

<400> SEQUENCE: 67

Val Asp Asn Lys Phe Asn Lys Glu Trp His Asp Ala Leu Arg Glu Ile
 1               5                  10                  15

His Arg Leu Pro Asn Leu Asn Val Tyr Gln Ser Leu Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 68
<211> LENGTH: 58
<212> TYPE: PRT
<213> ORGANISM: Artificial Sequence
<220> FEATURE:
<223> OTHER INFORMATION: Engineered Sequence

<400> SEQUENCE: 68

Val Asp Asn Lys Phe Asn Lys Glu Leu Tyr Tyr Ala Lys Leu Glu Ile
 1               5                  10                  15

Ala Asn Leu Pro Asn Leu Asn Val His Gln Trp Tyr Ala Phe Ile Ile
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 69
<211> LENGTH: 58
<212> TYPE: PRT
<213> ORGANISM: Artificial Sequence
<220> FEATURE:
<223> OTHER INFORMATION: Engineered Sequence

<400> SEQUENCE: 69

Val Asp Asn Lys Phe Asn Lys Glu Val Arg Phe Ala Ile Gly Glu Ile
 1               5                  10                  15

Gly Gly Leu Pro Asn Leu Asn Asp Arg Gln Leu Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 70
<211> LENGTH: 58
<212> TYPE: PRT
<213> ORGANISM: Artificial Sequence
<220> FEATURE:
<223> OTHER INFORMATION: Engineered Sequence

<400> SEQUENCE: 70

Val Asp Asn Lys Phe Asn Lys Glu Trp Glu Trp Ala Ser Lys Glu Ile
 1               5                  10                  15
```

Val Ile Leu Pro Asn Leu Asn Thr Gln Gln Arg Ala Ala Phe Ile Arg
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 71
<211> LENGTH: 58
<212> TYPE: PRT
<213> ORGANISM: Artificial Sequence
<220> FEATURE:
<223> OTHER INFORMATION: Engineered Sequence

<400> SEQUENCE: 71

Val Asp Asn Lys Phe Asn Lys Glu Thr Ala Arg Ala Thr Gly Glu Ile
1               5                   10                  15

Ala Gly Leu Pro Asn Leu Asn Ile Val Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 72
<211> LENGTH: 58
<212> TYPE: PRT
<213> ORGANISM: Artificial Sequence
<220> FEATURE:
<223> OTHER INFORMATION: Engineered Sequence

<400> SEQUENCE: 72

Val Asp Asn Lys Phe Asn Lys Glu Gly Arg Asn Ala Val Trp Glu Ile
1               5                   10                  15

Ala Glu Leu Pro Asn Leu Asn Leu His Gln Tyr Tyr Ala Phe Ile Thr
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 73
<211> LENGTH: 58
<212> TYPE: PRT
<213> ORGANISM: Artificial Sequence
<220> FEATURE:
<223> OTHER INFORMATION: Engineered Sequence

<400> SEQUENCE: 73

Val Asp Asn Lys Phe Asn Lys Glu Thr Ala Gln Ala Pro Leu Glu Ile
1               5                   10                  15

Ala Leu Leu Pro Asn Leu Asn Trp Pro Gln Lys Val Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 74
<211> LENGTH: 58
<212> TYPE: PRT
<213> ORGANISM: Artificial Sequence -continued

```
<220> FEATURE:
<223> OTHER INFORMATION: Engineered Sequence

<400> SEQUENCE: 74

Val Asp Asn Lys Phe Asn Lys Glu Val Phe Trp Ala Ala Gly Glu Ile
1               5                   10                  15

Gly Ile Leu Pro Asn Leu Asn His Met Gln Tyr Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 75
<211> LENGTH: 58
<212> TYPE: PRT
<213> ORGANISM: Artificial Sequence
<220> FEATURE:
<223> OTHER INFORMATION: Engineered Sequence

<400> SEQUENCE: 75

Val Asp Asn Lys Phe Asn Lys Glu Gln Leu Ser Ala Met Leu Glu Ile
1               5                   10                  15

Thr Arg Leu Pro Asn Leu Asn Thr Ala Gln Arg Pro Ala Phe Ile Trp
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 76
<211> LENGTH: 58
<212> TYPE: PRT
<213> ORGANISM: Artificial Sequence
<220> FEATURE:
<223> OTHER INFORMATION: Engineered Sequence

<400> SEQUENCE: 76

Val Asp Asn Lys Phe Asn Lys Glu Leu Gly Trp Ala Ile Gly Glu Ile
1               5                   10                  15

Gly Thr Leu Pro Asn Leu Asn His Gln Gln Phe Arg Ala Phe Ile Leu
            20                  25                  30

Ser Leu Trp Val Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 77
<211> LENGTH: 58
<212> TYPE: PRT
<213> ORGANISM: Artificial Sequence
<220> FEATURE:
<223> OTHER INFORMATION: Engineered Sequence

<400> SEQUENCE: 77

Val Asp Asn Lys Phe Asn Lys Glu Asn Ala Arg Ala Ile Glu Glu Ile
1               5                   10                  15

Ile Thr Leu Pro Asn Leu Asn Lys Thr Gln Arg Ala Ala Phe Ile Ser
            20                  25                  30

Ser Leu Thr Asp Asp Pro Ser Gln Ser Ala Asn Leu Leu Ala Glu Ala
        35                  40                  45
```

Lys Lys Leu Asn Asp Ala Gln Ala Pro Lys
    50                  55

<210> SEQ ID NO 78
<211> LENGTH: 58
<212> TYPE: PRT
<213> ORGANISM: Artificial Sequence
<220> FEATURE:
<223> OTHER INFORMATION: Engineered Sequence

<400> SEQUENCE: 78

Val Asp Asn Lys Phe Asn Lys Glu Gly Pro Gly Ala Val His Glu Ile
1               5                   10                  15

Val Arg Leu Pro Asn Leu Asn Pro Thr Gln Arg Val Ala Phe Ile Tyr
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 79
<211> LENGTH: 58
<212> TYPE: PRT
<213> ORGANISM: Artificial Sequence
<220> FEATURE:
<223> OTHER INFORMATION: Engineered Sequence

<400> SEQUENCE: 79

Val Asp Asn Lys Phe Asn Lys Glu Ser Leu Val Ala Ala Arg Glu Ile
1               5                   10                  15

Gly Val Leu Pro Asn Leu Asn Ser Ser Gln Lys Lys Ala Phe Ile Glu
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 80
<211> LENGTH: 58
<212> TYPE: PRT
<213> ORGANISM: Artificial Sequence
<220> FEATURE:
<223> OTHER INFORMATION: Engineered Sequence

<400> SEQUENCE: 80

Val Asp Asn Lys Phe Asn Lys Glu Ala Gly Val Ala Val Gly Glu Ile
1               5                   10                  15

Gly Met Leu Pro Asn Leu Asn Ala Leu Gln Lys Gly Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 81
<211> LENGTH: 58
<212> TYPE: PRT
<213> ORGANISM: Artificial Sequence
<220> FEATURE:
<223> OTHER INFORMATION: Engineered Sequence

<400> SEQUENCE: 81

Val Asp Asn Lys Phe Asn Lys Glu Ser Ala Cys Ala Thr Val Glu Ile

```
                     1               5                  10                 15
Gly Asn Leu Pro Asn Leu Asn Leu Ala Gln Tyr Arg Ala Phe Ile Leu
                 20                 25                 30

Ser Leu Arg Asp Asp Pro Ser Gln Ser Ala Asn Leu Leu Ala Glu Ala
             35                 40                 45

Lys Lys Leu Asn Asp Ala Gln Ala Pro Lys
         50                 55
```

<210> SEQ ID NO 82
<211> LENGTH: 58
<212> TYPE: PRT
<213> ORGANISM: Artificial Sequence
<220> FEATURE:
<223> OTHER INFORMATION: Engineered Sequence

<400> SEQUENCE: 82

```
Val Asp Asn Lys Phe Asn Lys Glu Lys Arg Pro Ala Asp Cys Glu Ile
1               5                  10                 15

Trp Ser Leu Pro Asn Leu Asn Arg Ser Gln Cys Phe Ala Phe Ile Lys
                 20                 25                 30

Ser Leu Arg Asp Asp Pro Ser Gln Ser Ala Asn Leu Leu Ala Glu Ala
             35                 40                 45

Lys Lys Leu Asn Asp Ala Gln Ala Pro Lys
         50                 55
```

<210> SEQ ID NO 83
<211> LENGTH: 58
<212> TYPE: PRT
<213> ORGANISM: Artificial Sequence
<220> FEATURE:
<223> OTHER INFORMATION: Engineered Sequence

<400> SEQUENCE: 83

```
Val Asp Asn Lys Phe Asn Lys Glu Thr Gly Arg Ala Val Gly Glu Ile
1               5                  10                 15

Gly Phe Leu Pro Asn Leu Asn Ala Tyr Gln Ala Ser Val Phe Ile Arg
                 20                 25                 30

Ser Leu Trp Asp Asp Pro Ser Gln Ser Ala Asn Leu Leu Ala Glu Ala
             35                 40                 45

Lys Lys Leu Asn Asp Ala Gln Ala Pro Lys
         50                 55
```

<210> SEQ ID NO 84
<211> LENGTH: 58
<212> TYPE: PRT
<213> ORGANISM: Artificial Sequence
<220> FEATURE:
<223> OTHER INFORMATION: Engineered Sequence

<400> SEQUENCE: 84

```
Val Asp Asn Lys Phe Asn Lys Glu Gly His Met Ala Thr Val Glu Ile
1               5                  10                 15

Ala Thr Leu Pro Asn Leu Asn Gly Ala Gln Lys Lys Ala Phe Ile Glu
                 20                 25                 30

Ser Leu Phe Asp Asp Pro Ser Gln Ser Ala Asn Leu Leu Ala Glu Ala
             35                 40                 45

Lys Lys Leu Asn Asp Ala Gln Ala Pro Lys
         50                 55
```

<210> SEQ ID NO 85
<211> LENGTH: 157

```
<212> TYPE: PRT
<213> ORGANISM: Artificial Sequence
<220> FEATURE:
<223> OTHER INFORMATION: Recombinant Protein

<400> SEQUENCE: 85

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
             20                  25                  30

Ala Asn Ala Leu Leu Ala Asn Gly Val Glu Leu Arg Asp Asn Gln Leu
         35                  40                  45

Val Val Pro Ser Glu Gly Leu Tyr Leu Ile Tyr Ser Gln Val Leu Phe
     50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                 85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 86
<211> LENGTH: 24
<212> TYPE: DNA
<213> ORGANISM: Artificial Sequence
<220> FEATURE:
<223> OTHER INFORMATION: Engineered sequence

<400> SEQUENCE: 86
tgcttccggc tcgtatgttg tgtg                                          24

<210> SEQ ID NO 87
<211> LENGTH: 21
<212> TYPE: DNA
<213> ORGANISM: Artificial Sequence
<220> FEATURE:
<223> OTHER INFORMATION: Engineered sequence

<400> SEQUENCE: 87
cggaaccaga gccaccaccg g                                             21

<210> SEQ ID NO 88
<211> LENGTH: 21
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (1)...(1)
<223> OTHER INFORMATION: Biotinylation

<400> SEQUENCE: 88
cggaaccaga gccaccaccg g                                             21

<210> SEQ ID NO 89
<211> LENGTH: 19
```

```
<212> TYPE: DNA
<213> ORGANISM: Artificial Sequence
<220> FEATURE:
<223> OTHER INFORMATION: Engineered sequence

<400> SEQUENCE: 89
gctagttatt gctcagcgg                                               19

<210> SEQ ID NO 90
<211> LENGTH: 23
<212> TYPE: DNA
<213> ORGANISM: Artificial Sequence
<220> FEATURE:
<223> OTHER INFORMATION: Engineered sequence

<400> SEQUENCE: 90 aaaggggat gtgctgcaag gcg                                           23

<210> SEQ ID NO 91
<211> LENGTH: 18
<212> TYPE: DNA
<213> ORGANISM: Artificial Sequence
<220> FEATURE:
<223> OTHER INFORMATION: Engineered sequence

<400> SEQUENCE: 91
ccagtaaggc aaccccgc                                                18

<210> SEQ ID NO 92
<211> LENGTH: 20
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (1)...(1)
<223> OTHER INFORMATION: Biotinylation

<400> SEQUENCE: 92 caaaaaccc ctcaagaccc                                               20

<210> SEQ ID NO 93
<211> LENGTH: 17
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (1)...(1)
<223> OTHER INFORMATION: Biotinylation

<400> SEQUENCE: 93
gggctttgtt agcagcc                                                 17

<210> SEQ ID NO 94
<211> LENGTH: 19
<212> TYPE: DNA
<213> ORGANISM: Artificial Sequence
<220> FEATURE:
<223> OTHER INFORMATION: Engineered sequence

<400> SEQUENCE: 94
cccgcgaaat taatacgac                                               19

<210> SEQ ID NO 95
<211> LENGTH: 24
```

```
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (1)...(1)
<223> OTHER INFORMATION: Biotinylation

<400> SEQUENCE: 95
tgcttccggc tcgtatgttg tgtg                                              24

<210> SEQ ID NO 96
<211> LENGTH: 129
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (31)...(32)
<223> OTHER INFORMATION: n is a, c, g, or t
<220> FEATURE:
<221> NAME/KEY: misc_feature
<222> LOCATION: (34)...(35)
<223> OTHER INFORMATION: n is a, c, g, or t
<220> FEATURE:
<221> NAME/KEY: misc_feature
<222> LOCATION: (37)...(38)
<223> OTHER INFORMATION: n is a, c, g, or t
<220> FEATURE:
<221> NAME/KEY: misc_feature
<222> LOCATION: (43)...(44)
<223> OTHER INFORMATION: n is a, c, g, or t
<220> FEATURE:
<221> NAME/KEY: misc_feature
<222> LOCATION: (46)...(47)
<223> OTHER INFORMATION: n is a, c, g, or t
<220> FEATURE:
<221> NAME/KEY: misc_feature
<222> LOCATION: (55)...(56)
<223> OTHER INFORMATION: n is a, c, g, or t
<220> FEATURE:
<221> NAME/KEY: misc_feature
<222> LOCATION: (58)...(59)
<223> OTHER INFORMATION: n is a, c, g, or t
<220> FEATURE:
<221> NAME/KEY: misc_feature
<222> LOCATION: (76)...(77)
<223> OTHER INFORMATION: n is a, c, g, or t
<220> FEATURE:
<221> NAME/KEY: misc_feature
<222> LOCATION: (79)...(80)
<223> OTHER INFORMATION: n is a, c, g, or t
<220> FEATURE:
<221> NAME/KEY: misc_feature
<222> LOCATION: (85)...(86)
<223> OTHER INFORMATION: n is a, c, g, or t
<220> FEATURE:
<221> NAME/KEY: misc_feature
<222> LOCATION: (88)...(89)
<223> OTHER INFORMATION: n is a, c, g, or t
<220> FEATURE:
<221> NAME/KEY: misc_feature
<222> LOCATION: (100)...(101)
<223> OTHER INFORMATION: n is a, c, g, or t
<220> FEATURE:
<221> NAME/KEY: misc_feature
<222> LOCATION: (109)...(110)
<223> OTHER INFORMATION: n is a, c, g, or t

<400> SEQUENCE: 96
ctcgaggtag acaacaaatt caacaaagaa nnknnknnkg cgnnknnkga gatcnnknnk        60
ttacctaact taaacnnknn kcaannknnk gccttcatcn nkagtttann kgatgaccca       120
agccaaagc                                                              129
```

```
<210> SEQ ID NO 97
<211> LENGTH: 19
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (1)...(1)
<223> OTHER INFORMATION: Biotinylation

<400> SEQUENCE: 97
caataaacca gccagccgg                                                   19

<210> SEQ ID NO 98
<211> LENGTH: 22
<212> TYPE: DNA
<213> ORGANISM: Artificial Sequence
<220> FEATURE:
<223> OTHER INFORMATION: Engineered sequence

<400> SEQUENCE: 98
aataaaccag ccagccggaa gg                                               22

<210> SEQ ID NO 99
<211> LENGTH: 32
<212> TYPE: DNA
<213> ORGANISM: Artificial Sequence
<220> FEATURE:
<223> OTHER INFORMATION: Engineered sequence

<400> SEQUENCE: 99
cccccccccc tcgaggtaga caacaaattc aa                                    32

<210> SEQ ID NO 100
<211> LENGTH: 39
<212> TYPE: DNA
<213> ORGANISM: Artificial Sequence
<220> FEATURE:
<223> OTHER INFORMATION: Engineered sequence

<400> SEQUENCE: 100
cccccctgct agcaagttag cgctttggct tgggtcatc                             39
```